(12) United States Patent
Buchanan et al.

(10) Patent No.: US 12,064,099 B2
(45) Date of Patent: Aug. 20, 2024

(54) DELIVERY AND ASSESSMENT AIDS FOR IMPLANTS

(71) Applicants: W. L. Gore & Associates, Inc., Newark, DE (US); Mayo Foundation for Medical Education and Research, Rochester, MN (US)

(72) Inventors: Brendan S. Buchanan, Flagstaff, AZ (US); Benjamin I. Espen, Flagstaff, AZ (US); Reed A. Houge, Flagstaff, AZ (US); Allan B. Dietz, Chatfield, MN (US); William A. Faubion, Jr., Rochester, MN (US); Eric J. Dozois, Rochester, MN (US)

(73) Assignees: W. L. Gore & Associates, Inc., Newark, DE (US); Mayo Foundation for Medical Education and Research, Rochester, MN (US)

( * ) Notice: Subject to any disclaimer, the term of this patent is extended or adjusted under 35 U.S.C. 154(b) by 168 days.

(21) Appl. No.: 17/482,101

(22) Filed: Sep. 22, 2021

(65) Prior Publication Data
US 2023/0086502 A1 Mar. 23, 2023
US 2023/0404558 A9 Dec. 21, 2023

Related U.S. Application Data

(60) Provisional application No. 63/082,233, filed on Sep. 23, 2020.

(51) Int. Cl.
*A61B 17/00* (2006.01)
(52) U.S. Cl.
CPC .............. *A61B 17/0057* (2013.01); *A61B 2017/00004* (2013.01); *A61B 2017/00477* (2013.01);
(Continued)

(58) Field of Classification Search
CPC .......... A61B 2017/00004; A61B 2017/00477; A61B 2017/00641; A61B 2017/00646
See application file for complete search history.

(56) References Cited

U.S. PATENT DOCUMENTS 5,061,274 A * 10/1991 Kensey .............. A61B 17/0057
604/15
5,484,426 A * 1/1996 Yoon .................. A61B 17/0218
604/11
(Continued)

FOREIGN PATENT DOCUMENTS

CN 2203612 Y 7/1995
CN 2219131 Y 2/1996
(Continued)

OTHER PUBLICATIONS

International Search Report and Written Opinion received for PCT Patent Application No. PCT/US21/51765, mailed on Jan. 19, 2022, 14 pages.

*Primary Examiner* — Alexander J Orkin

(57) ABSTRACT

A treatment system includes an insert that is resiliently deflectable. The tip portion of the insert can be configured to be coupled to the trailing portion of an implant. A guide tube having an internal lumen is configured to permit passage of the tip portion and the body portion of the insert through a guide tube. The guide tube can have a length that is less than that of the insert. Treatment systems include a plurality of inserts, each insert differing from in at least one of length, diameter, and curvature. Treating a patient can include sizing a fistula using an insert.

25 Claims, 16 Drawing Sheets

(52) U.S. Cl.
CPC ............... *A61B 2017/00641* (2013.01); *A61B 2017/00646* (2013.01)

(56) References Cited

U.S. PATENT DOCUMENTS

| | | | |
|---|---|---|---|
| 5,584,827 A * | 12/1996 | Korteweg | A61F 13/126 604/11 |
| 5,730,756 A * | 3/1998 | Kieturakis | A61F 2/0063 606/190 |
| 6,245,090 B1 * | 6/2001 | Gilson | A61B 17/12022 606/213 |
| 2005/0155608 A1 * | 7/2005 | Pavcnik | A61B 17/0057 128/831 |
| 2005/0216040 A1 | 9/2005 | Gertner et al. | |
| 2006/0015142 A1 * | 1/2006 | Malazgirt | A61F 2/0063 606/213 |
| 2007/0179507 A1 * | 8/2007 | Shah | A61B 50/30 606/113 |
| 2007/0248640 A1 * | 10/2007 | Karabey | A61B 17/0057 424/423 |
| 2008/0027477 A1 | 1/2008 | Obermiller et al. | |
| 2008/0051831 A1 | 2/2008 | Deal et al. | |
| 2008/0154286 A1 * | 6/2008 | Abbott | A61B 17/0483 606/228 |
| 2009/0054927 A1 | 2/2009 | Agnew | |
| 2010/0070015 A1 | 3/2010 | Schneider et al. | |
| 2010/0076463 A1 | 3/2010 | Mavani et al. | |
| 2011/0282337 A1 | 11/2011 | Hall et al. | |
| 2011/0288581 A1 | 11/2011 | Paul, Jr. et al. | |
| 2012/0035644 A1 * | 2/2012 | Eskaros | A61B 17/0057 606/198 |
| 2012/0323271 A1 | 12/2012 | Obermiller et al. | |
| 2013/0158594 A1 * | 6/2013 | Carrison | A61B 17/0057 606/213 |
| 2014/0081318 A1 | 3/2014 | Houser et al. | |
| 2014/0277116 A1 | 9/2014 | Stanley et al. | |
| 2014/0303603 A1 | 10/2014 | Kullas et al. | |
| 2016/0000416 A1 | 1/2016 | Carrison et al. | |
| 2016/0296382 A1 * | 10/2016 | Spillane | A61F 13/36 |
| 2017/0086808 A1 | 3/2017 | Patel et al. | |
| 2019/0365365 A1 | 12/2019 | Bippart et al. | |
| 2020/0022689 A1 | 1/2020 | Seedhom et al. | |

FOREIGN PATENT DOCUMENTS

| | | |
|---|---|---|
| CN | 2362498 Y | 2/2000 |
| CN | 106859734 A | 6/2017 |
| CN | 209611207 U | 11/2019 |
| JP | 2007-530147 A | 11/2007 |
| JP | 2011-045738 A | 3/2011 |
| JP | 2012-501803 A | 1/2012 |
| JP | 6197985 B2 | 9/2017 |
| WO | 2016/141174 A1 | 9/2016 |
| WO | 2018/175624 A1 | 9/2018 |

\* cited by examiner

DELIVERY AND ASSESSMENT AIDS FOR IMPLANTS

CROSS-REFERENCE TO RELATED APPLICATION

This application claims the benefit of Provisional Application No. 63/082,233, filed Sep. 23, 2020, which is incorporated herein by reference in its entirety for all purposes.

BACKGROUND

Various types of wounds may not heal without intervention, or not heal quickly enough without substantial complications. One such wound, a fistula tract, which can occur in the anal canal (anal fistula), is the result of either an infection in an anal gland, or severe inflammation secondary to inflammatory bowel disease, that will generally not heal on its own and must be treated before secondary complications arise. While fistulas can express in a variety of forms, in general terms, an anal fistula is typically a small opening, or path that develops somewhere between anal canal or rectum of a patient and tissue at or around the anus. Treatment of anal fistulas can be challenging for a variety of reasons, often times requiring some level of compromise between treatment of the fistula and maintenance of fecal continence. More traditional treatments include a fistulotomy that may damage the anal sphincter and contribute to worsening fecal incontinence or management of drainage using a seton in the hope the body can heal itself. The GORE® BIO-A® Fistula Plug was proposed as an alternative to the fistulotomy and seton techniques, taking the form of a bioabsorbable device implanted into the fistula to provide a scaffold for soft tissue repair and facilitate closure of the anal fistula. Studies revealed substantial enhancements to implant therapeutic effect by combining mesenchymal stem cells with such implants, and in particular with the GORE® BIO-A® Fistula Plug. See, e.g., International Patent Application Publication WO2018/175624 to Mayo Foundation for Medical Education and Research, filed Mar. 21, 2018 and entitled "Methods and Materials for Treating Fistulas" and also Dietz et al., "Autologous Mesenchymal Stem Cells, Applied in a Bioabsorbable Matrix, for Treatment of Perianal Fistulas in Patients With Crohn's Disease," 153 Gastroenterology 1, pages 59-62 (July 2017).

SUMMARY

Various inventive concepts addressed in this patent specification relate to treatment systems and methods for effective assessment of, and delivery of implants for treating, wounds such as anal fistulas. Some of the inventive features provided by such implant delivery and site assessment systems and methods may be particularly beneficial in the context of implants with relatively delicate, fragile and/or wet coatings, treatments, or other features (e.g., deposited cell, cell-derived, cellular product, or hydrolysable materials), and/or in technically challenging patient anatomy, although any of a variety of implants, treatment types, and patients may benefit from the systems and techniques addressed herein. Various attendant features and/or advantages of systems and techniques addressed in this specification include atraumatic implant delivery (e.g., a bioabsorbable implant carrying mesenchymal stem cells) and/or effective treatment site assessment (e.g., fistula tract assessment), as well as reduced risk of defeating efficacy and integrity of the implant (e.g., which may otherwise be propagated through mechanical engagement of the implant with tissue, the implanting physician, or otherwise). Additional advantages may include more standardized implantation and/or assessment techniques, reduced tissue manipulation and engagement during implantation and/or wound assessment, among others.

According to one example ("Example 1"), a treatment system includes an insert that is resiliently deflectable, the insert extending between a tip portion and a control portion, with a body portion located between the tip portion and the control portion, the tip portion and the body portion combining to define an insert length of the insert. The tip portion of the insert can be configured to be coupled to the trailing portion of an implant. The treatment system includes a guide tube having an internal lumen. The guide tube is configured to permit passage of the tip portion and the body portion of the insert through the guide tube, the guide tube having a guide tube length that is less than the insert length.

According to another example ("Example 2"), further to Example 1 at least one of the tip portion and the body portion includes an abrasion feature.

According to another example ("Example 3"), further to Examples 1 or 2, at least one of the body portion and the control portion includes a depth indicator feature.

According to another example ("Example 4"), further to any preceding Example, the body portion has a variable diameter.

According to another example ("Example 5"), further to any preceding Example, the treatment system further includes a source of a treatment medium (e.g., water, saline, peroxide, or medicament) in fluid communication with at least one of the tip portion and the body portion and, optionally, wherein at least one of the tip portion and the body portion includes one or more apertures for delivering the treatment medium into a body of a patient.

According to another example ("Example 6"), further to any preceding Example, the body portion is configured to bend 180 degrees without kinking.

According to another example ("Example 7"), further to any preceding Example, the tip portion has a tapered to a free end.

According to another example ("Example 8"), further to any preceding Example, the body portion is configured to be resiliently deflectable.

According to another example ("Example 9"), further to any preceding Example, further comprising an implant having a leading portion and a trailing portion and, optionally, wherein the trailing portion has an enlarged outer profile relative to the leading portion.

According to another example ("Example 10"), further to Example 9, the trailing portion of the implant is disc-shaped.

According to another example ("Example 11"), further to Examples 9 or 10, the leading portion of the implant includes a plurality of legs.

According to another example ("Example 12"), further to any of Examples 9 to 11, the implant includes a carrier component (e.g., formed of a bioabsorbable material, tissue-derived material) and, optionally, a second component (e.g., active ingredient, cell material, cell-derived material, cellular product material, or hydrolysable material) carried by the carrier component.

According to another example ("Example 13"), further to any of Examples 9 to 12, the tip portion of the insert includes an entanglement feature configured to releasably couple to the implant.

According to another example ("Example 14"), further to any of Examples 9 to 12, the tip portion of the insert includes an eyelet feature configured to receive a filament coupling the implant to the tip portion and, optionally, wherein the eyelet is formed as an aperture through material of the tip portion or by an adjustable loop.

According to another example ("Example 15"), further to any of Examples 9 to 12, wherein the tip portion of the insert includes a hook feature configured to receive a filament coupling the implant to the tip portion.

According to another example ("Example 16"), further to any preceding Example, the guide tube is substantially more flexible than the insert.

According to another example ("Example 17"), further to any preceding Example, the body portion of the insert exhibits a flexural modulus between 100 and 500 MPa.

According to another example ("Example 18"), further to any preceding Example, the guide tube exhibits a flexural modulus between 100 and 500 MPa.

According to another example ("Example 19"), further to any preceding Example, the body portion is characterized by a buckling force of at least 5 N.

According to another example ("Example 20"), a method of treating a patient includes directing an insert through a fistula; placing a guide tube over the insert either prior to or after directing the insert through the fistula such that a tip portion of the insert projects from the guide tube; coupling an implant to the tip portion of the insert; retracting the insert such that the implant is pulled into the guide tube; decoupling the implant and the insert; and removing the guide tube from the fistula.

According to another example ("Example 21"), further to the Example of claim 20, directing the insert through the fistula includes tracking a tortuosity of the fistula with the insert.

According to another example ("Example 22"), further to Example 21, the fistula has a first end and a second end and the tortuosity of the fistula is characterized by a tortuosity ratio defined as a ratio of a length of the fistula between the first and second end to a straight-line distance the first and second ends of the fistula, and further wherein the tortuosity ratio is at least 2.

According to another example ("Example 23"), further to Example 22, coupling the implant to the insert includes connecting a coupling element (e.g., suture, filament, or line) between the tip portion of the insert and the implant.

According to another example ("Example 24"), further to any of Examples 20 to 23, the implant includes a leading portion and a trailing portion, the trailing portion having an enlarged profile relative to the leading portion, and further wherein the step of coupling the implant to the insert includes coupling the leading portion to the tip portion of the insert.

According to another example ("Example 25"), further to any of Examples 20 to 24, wherein the fistula has a first end at an internal body location and a second end at an external body location, and further wherein the enlarged profile of the trailing portion is seated at the second end of the fistula following retraction of the insert.

According to another example ("Example 26"), further to any of Examples 20 to 25, retracting the insert such that the insert is pulled into the guide tube includes drawing the trailing portion of the implant into the guide tube prior to removing the guide tube from the fistula.

According to another example ("Example 27"), further to any of Examples 20 to 26, the method further includes introducing the leading portion of the implant into a body of a patient prior to coupling the implant to the tip portion of the insert.

According to another example ("Example 28"), a treatment system includes a plurality of inserts, each insert differing from in at least one of length and diameter, that is resiliently deflectable, the insert extending between a tip portion and a control portion, with a body portion located between the tip portion and the control portion. The tip portion and the body portion combining to define an insert length of the insert. The tip portion of the insert can be configured to be coupled to the trailing portion of an implant. The treatment system also can include a guide tube having an internal lumen that is configured to permit passage of the tip portion and the body portion through the guide tube. The guide tube has a guide tube length that is less than the insert length and the guide tube being more flexible than the body portion of the insert.

According to another example ("Example 29"), the tip portion includes at least one of an eyelet, a hook, and a loop configured for coupling a filament to the tip portion.

According to another example ("Example 30"), a treatment system includes a plurality of inserts each having at least one of a different diameter, length, and curvature than another one of the plurality of inserts, each insert being resiliently deflectable and extending between a tip portion and a control portion, with a body portion located between the tip portion and the control portion, the tip portion and the body portion combining to define an insert length, the tip portion being configured to be coupled to the trailing portion of an implant.

According to another example ("Example 31"), further to Example 30, the system includes a guide tube having an internal lumen, the guide tube having a guide tube length that is less than the insert length of, and being configured to permit passage of the tip portion and the body portion of at least one of the plurality of inserts.

According to another example ("Example 32"), further to Examples 30 or 31, the system includes a plurality of implants having at least one of a different diameter, length, and curvature than another one of the plurality of implants.

According to another example ("Example 33"), a method of treating a patient includes sizing a fistula using an insert that is resiliently deflectable and extends between a tip portion and a control portion, with a body portion located between the tip portion and the control portion, the tip portion and the body portion combining to define an insert length, sizing the fistula including inserting the insert into a fistula to make an assessment of the fit of the insert in the fistula.

According to another example ("Example 34"), further to Example 33, sizing the fistula further includes inserting a plurality of inserts into the fistula to make an assessment the fit of the plurality of inserts in the fistula, the plurality of inserts each having at least one of a different diameter, length, and curvature than another one of the plurality of inserts.

According to another example ("Example 35"), further to Examples 33 or 34, the method includes selecting an implant for implantation based upon the assessment; and implanting the implant that is selected based upon the assessment in the fistula.

According to another example ("Example 36"), a method of treating a patient comprises directing an insert through a wound tract; placing a guide tube over the insert either prior to or after directing the insert through the wound tract such that a tip portion of the insert projects from the guide tube; coupling an implant to the tip portion of the insert; retracting the insert such that the implant is pulled into the guide tube;

decoupling the implant and the insert; and removing the guide tube from the wound tract.

According to another example ("Example 37"), further to Example 36, directing the insert through the wound tract includes tracking a tortuosity of the wound tract with the insert.

According to another example ("Example 38"), further to Example 37, the wound tract has a first end and a second end and the tortuosity of the wound tract is characterized by a tortuosity ratio defined as a ratio of a length of the wound tract between the first and second end to a straight-line distance the first and second ends of the wound tract, and further wherein the tortuosity ratio is at least 2.

According to another example ("Example 39"), further to Example 38, coupling the implant to the insert includes connecting a coupling element (e.g., suture, filament, or line) between the tip portion of the insert and the implant.

According to another example ("Example 40"), further to Examples 36-39, the implant includes a leading portion and a trailing portion, the trailing portion having an enlarged profile relative to the leading portion, and further wherein the step of coupling the implant to the insert includes coupling the leading portion to the tip portion of the insert.

According to another example ("Example 41"), further to Examples 36-40, the wound tract has a first end at an internal body location and a second end at an external body location, and further wherein the enlarged profile of the trailing portion is seated at the second end of the wound tract following retraction of the insert.

According to another example ("Example 42"), further to Examples 36-41, retracting the insert such that the insert is pulled into the guide tube includes drawing the trailing portion of the implant into the guide tube prior to removing the guide tube from the wound tract.

According to another example ("Example 43"), further to Example 36-42, the method further comprises introducing the leading portion of the implant into a body of a patient prior to coupling the implant to the tip portion of the insert.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIGS. 1 and 2 show an insert, guide tube, and implant of the system.

FIG. 3 shows the insert and guide tube of the system.

FIG. 4 shows the guide tube and implant of the system.

DETAILED DESCRIPTION

Definitions and Terminology

This disclosure is not meant to be read in a restrictive manner. For example, the terminology used in the application should be read broadly in the context of the meaning those in the field would attribute such terminology.

The term "wound" is used broadly in the context of this specification to refer to a site or location targeted for assessment and potential treatment through use of an implant, delivery of a medicament, a surgical procedure, and combinations thereof.

The term "fistula" is generally used in this patent specification in the context of an anal fistula tract, although the term and concepts related thereto should be broadly construed to relate to any of a variety of tracts or pathways that may be targeted for assessment and/or treatment through use of the systems and techniques addressed in this specification.

Directional terminology (e.g., up, down, superior, inferior, distal, proximal and the like) is generally used to dictate the relationship or orientation of system components in a relative, rather than absolute sense, unless their use in context specifically dictates otherwise.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters, for example. In the event it is determined that individuals having ordinary skill in the relevant arts would not readily ascertain values for such reasonably small differences, the terms "about" and "approximately" can be understood to mean plus or minus 10% of the stated value.

Description of Various Embodiments

The description that follows references various features called out in the accompanying drawings. The intent is not that by such reference, the inventive scope of the concepts provided herewith are narrowed. Instead, those features are provided to exemplify, but not limit the scope of the ideas conveyed by this specification to those in the field. Along those lines, it should also be noted that the accompanying drawings, referenced as "figures," are not necessarily drawn to scale, but may be exaggerated to illustrate various aspects of the present disclosure, and in that regard, the drawings should not be construed as limiting.

Figure 1:
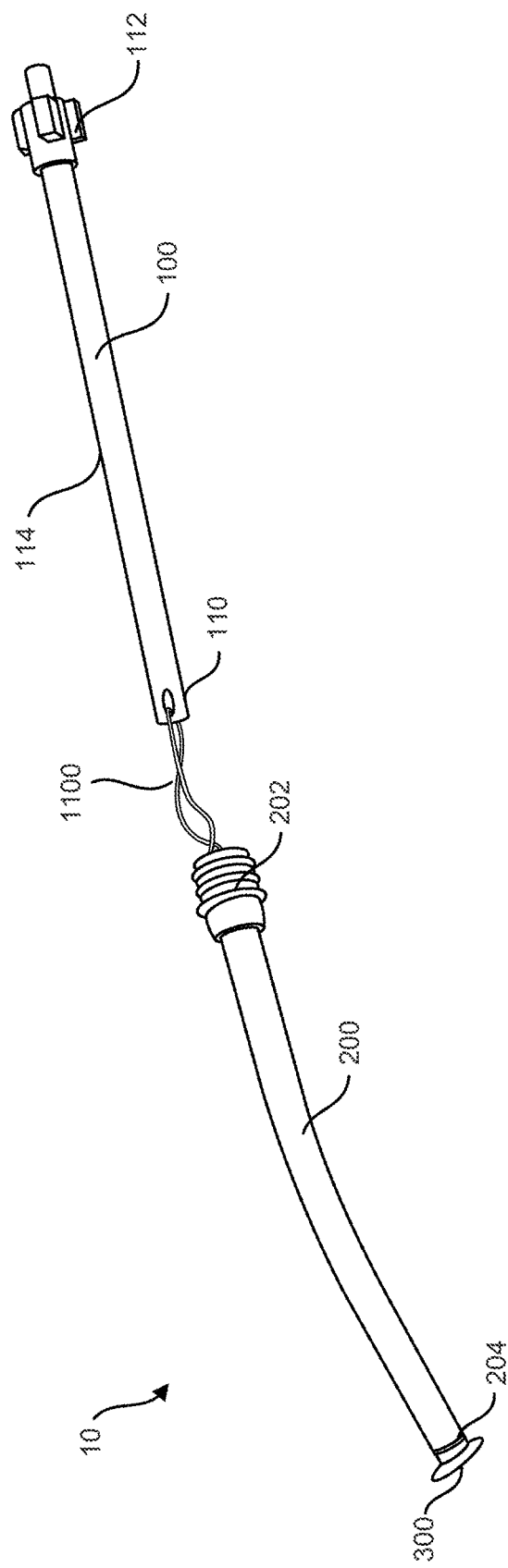
FIGS. 1 through 4 show components of a treatment system 10 in various states of assembly, according to some embodiments.
Figure 2:
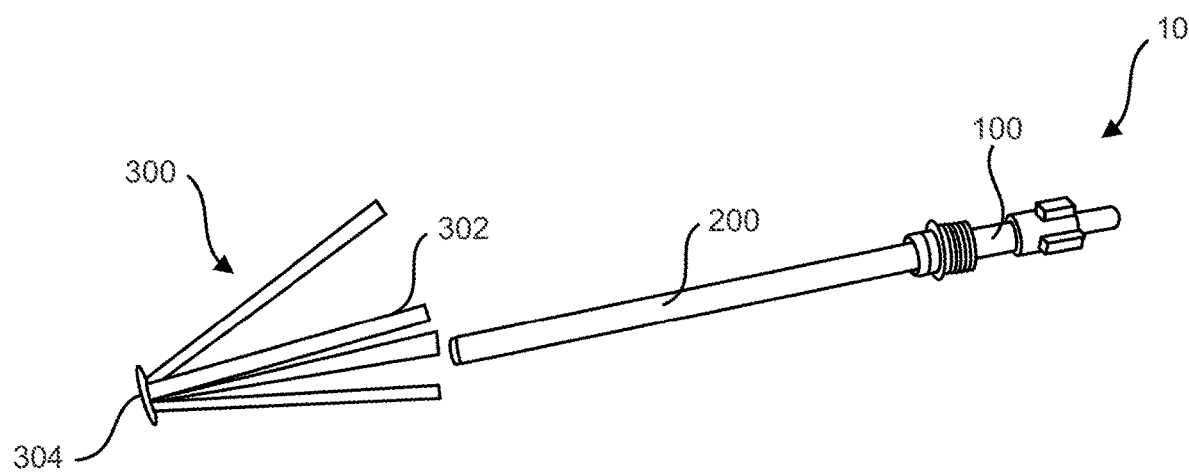
Figure 3:
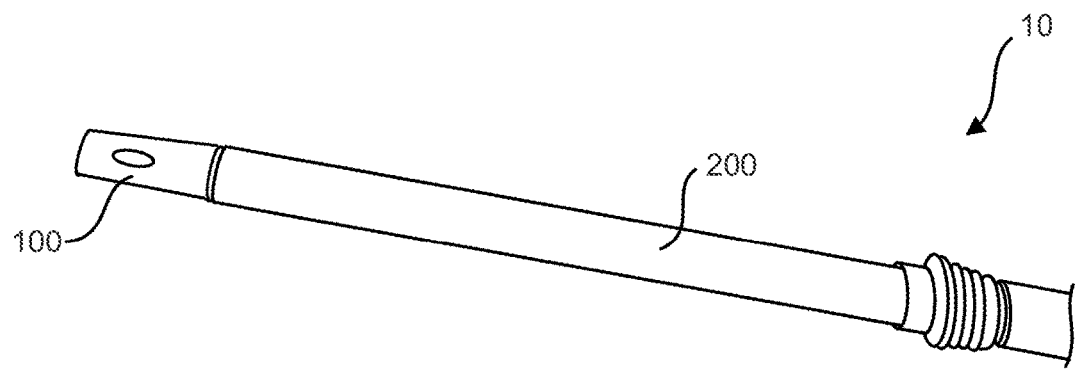
Figure 4:
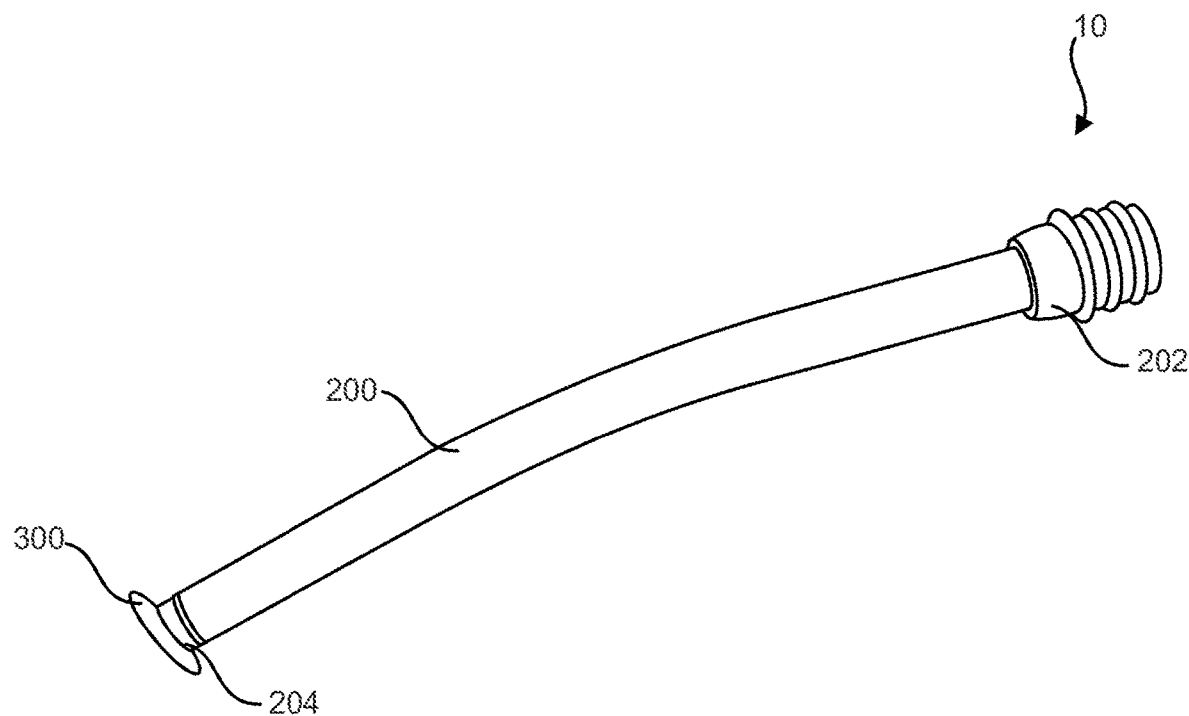

FIGS. 1 through 4 show components of a treatment system 10 in various states of assembly. As shown in FIG. 1, the treatment system 10 includes an insert 100, a guide tube 200, and an implant 300. Although a single insert 100, guide tube 200 and implant 300 are shown, as described in association with further examples, there may be a plurality of one or more of those components (e.g., having differing configurations) incorporated with the treatment system 10. As indicated in FIGS. 1 to 4, the guide tube 200 is configured to receive portions of the insert 100 and the implant 300, for example by drawing the implant 300 into the guide tube 200 with the insert 100. Though an exemplary operative sequence will be described in more detail, FIGS. 1 to 4 are described as follows: FIG. 1 shows the implant 300 fully withdrawn into the guide tube 200 with the insert 100 withdrawn from the guide tube 200; FIG. 2 shows the insert 100 inserted into the guide tube 200 prior to pulling the implant 300 into the guide tube 200; FIG. 3 shows the insert 100 fully inserted into the guide tube 200 prior to pulling the implant 300 (not shown) into the guide tube 200; and FIG. 4 shows the implant 300 fully withdrawn into the guide tube 200 and decoupled from the insert 100.

Figure 5:
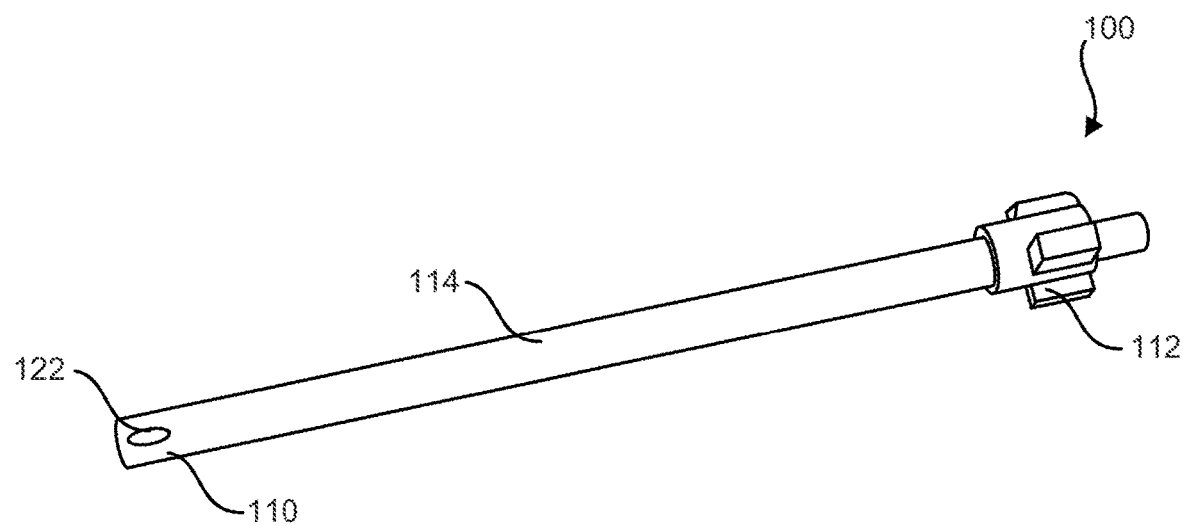
FIG. 5 shows the insert of the system.

FIG. 5 shows the insert 100 from an isometric, or perspective view. As shown, the insert 100 has a first end 102 and a second end 104 and extends between a tip portion 110 and a control portion 112, with a body portion 114 located between the tip portion 110 and the control portion 112. In general terms, the tip portion 110 is configured to be releasably coupled to the implant 300, the body portion 114 is configured to have sufficient column strength to be pushed, or inserted into a fistula tract but also resiliently deflect or conform to the tortuosity of the tract, and the control portion 112 is configured to be manipulated by a user (e.g., manually, or by hand) for insertion and retraction of the insert 100.

The tip portion 110 and the body portion 114 may be integrally formed, or formed as separate connected parts as desired. Suitable materials for the tip portion 110 and the body portion 114 generally include biocompatible materials, such as those generally associated with catheters and similar devices used to traverse pathways in the body of a patient. Some examples include nylon, polyether block amide, high density polyethylene, or others. The control portion 112 may be formed of similar or different materials than the tip portion 110 and the body portion 114. In various examples, the control portion 112 is generally more stiff, and may include grasping features, in comparison to the tip portion 110 and the body portion 114, to facilitate manipulation by a user of the insert 100.

As shown, the tip portion 110 extends from the body portion 114 to a free end 120. The tip portion 112 may be integrally formed with the body portion 114, as a single, monolithic unit or piece. The tip portion 110 is typically configured to be atraumatic and may have tapered and/or rounded end configurations to facilitate insertion into and through a fistula. Though the tip portion 110 is generally configured to be atraumatic, the tip portion 110 may function to widen, or enlarge one or more portions of a fistula tract in certain scenarios.

The tip portion 110 may be configured with one or more features configured to facilitate coupling to the implant 300, either directly or through a tensioning element coupled to the implant 300. FIG. 5 shows one example of a coupling feature 122, and FIGS. 6A to 6E show additional configurations for the coupling feature 122.

Figure 6A:
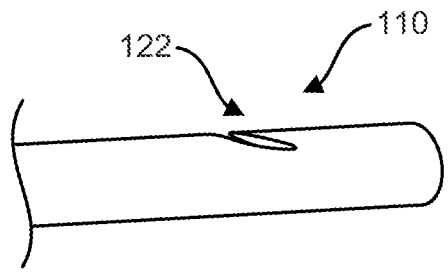
FIGS. 6A to 6G show various features and configurations of a tip portion of the insert of the system, according to some embodiments.

In the example of FIG. 5, the coupling feature 122 is configured as an aperture formed through the tip portion 110. The aperture shown is configured as a "closed" aperture in that it has a continuous boundary. A portion of the implant 300 can be received in the aperture or a tensioning element coupled to the implant 300 can be received therein (e.g., tied in the aperture). As shown in FIG. 6A, in another example the coupling feature 122 can also be configured as an "open" aperture, which can alternatively be described as a slot or pocket, that has a closed border at one end and opens to an outer surface of the tip portion 110 at another (e.g., opposite) end. In different terms, a "closed" aperture passes through the material of the tip portion 110 in a first direction, and has a discontinuous, or open border transverse to the first direction.

Figure 6B:
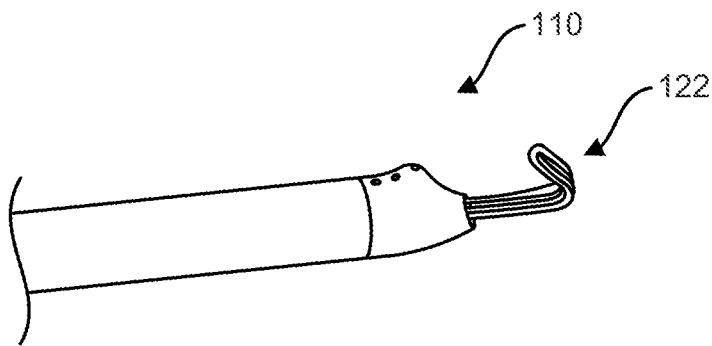

As shown in FIG. 6B, in another example the coupling feature 122 can be configured as a hook (e.g., optionally extendable or retractable relative to a surrounding part of the tip portion 110). The hook could be formed with a rounded end as shown to help ensure a more atraumatic configuration. In some examples, the hook is formed of a biocompatible metallic material (e.g., stainless steel) although a variety of materials may be used as desired. The coupling feature 122 with the hook configuration can capture the implant 300 directly or by capturing a tensioning element coupled to the implant 300. Additional grasping or hooking mechanisms are contemplated, such as clamping or grasping mechanisms for directly grasping the implant 300 (see FIG. 6C and description below).

Figure 6C:
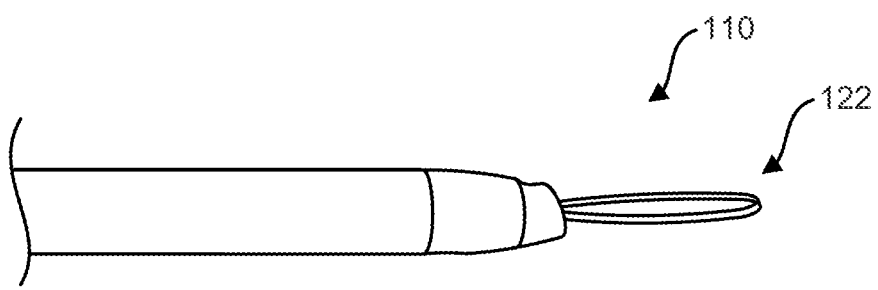

As shown in FIG. 6C, in still another example the coupling feature 122 can be configured as a loop (e.g., optionally extendable or retractable so that the loop is adjustable in diameter and/or length relative to a surrounding part of the tip portion 110). The loop can be used to capture a portion of the implant 300 directly, or to couple to a tensioning element attached thereto. With regard to terminology, the loop also forms an aperture, and as such the coupling feature 122 configuration in FIG. 6C may also be described as an adjustable aperture or adjustable aperture configuration. The loop may be formed with a rounded end as shown to help ensure a more atraumatic configuration. In some examples, the loop is formed of a biocompatible metallic material (e.g., stainless steel or nickel-titanium alloys) although a variety of materials may be used as desired.

Figure 6D:
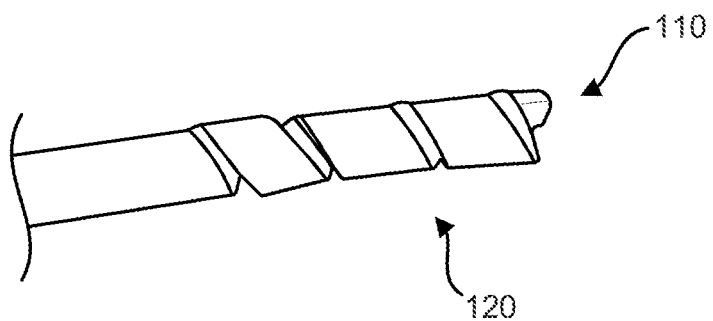

As shown in FIG. 6D, in other examples the coupling feature 122 is configured as an entanglement feature, such as a helically cut channel or relief formed in or coupled to adjacent parts of the tip portion 110. A user (not shown) may capture the implant 300 or a tensioning element coupled thereto (e.g., a fiber or filament, also not shown in FIG. 6D) by dragging the coupling feature 122 across the implant 300 or a tensioning element coupled thereto (e.g., a fiber or filament) or rotating the coupling feature 122 to cause the implant 300 or tensioning element to be entangled or trapped in the channel or relief feature.

Figure 6E:
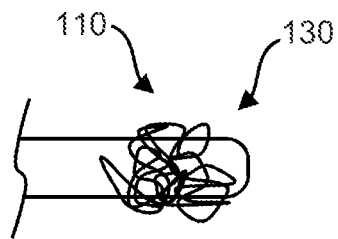

As shown in FIG. 6E, in other examples the coupling feature 122 is configured as an entanglement feature in the form of a fibrous mass formed in or coupled to adjacent parts of the tip portion 110. A user (not shown) may capture a tensioning element (e.g., a fiber or filament, also not shown in FIG. 6D) by dragging the coupling feature 122 across the fiber or filament, or rotating the coupling feature 122 to cause the fiber to be entangled or trapped in the fibrous mass.

Figure 6F:
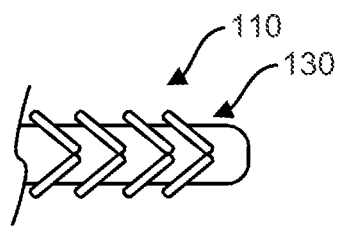

In some examples, the tip portion 110 includes a treatment feature 130. FIG. 6F shows one example of the treatment feature 130. As shown, the treatment feature 130 includes a plurality of flexible fingers, or projections that extend out radially from adjacent parts of the tip portion, and may optionally be angled in a proximal direction, toward the control portion 112 or in any angular orientation as desired. In some embodiments, the flexible fingers, or projections may be used in a cleansing, or clearing operation by inserting and/or retracting the treatment feature 130 within a fistula. The flexible fingers or projections may gently abrade, scrub, agitate, or otherwise engage the walls of the fistula to remove detritus, or other unwanted matter from the fistula, for example. Purposes other than cleansing may also be achieved by such action, including encouraging healing response, for example. Thus, the treatment feature 130 of FIG. 6F may alternatively be described as an abrasion, abrading, scrubbing, agitating, or cleansing feature as desired.

Figure 6G:
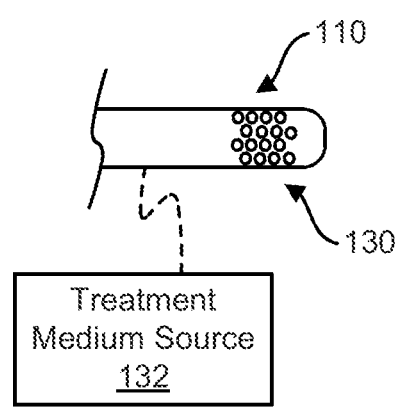

Another example configuration for the treatment feature 130 is shown in FIG. 6G, in the form of one or more fluid apertures (e.g., a plurality of fluid apertures in the tip portion 110). As shown, the treatment feature 130 may be in fluid communication with a treatment medium source 132 (e.g., containing water, saline, peroxide, or medicament). The treatment feature 130 may be coupled to the treatment medium source 132 via a variety of methods, but generally one or more lumens, channels, or other features associated with the insert 100 may form a conduit, or pathway from the treatment feature 130 to the treatment medium source 132. In some examples, the treatment medium source 132 is a syringe, or similar apparatus, that may be pressurized to delivery treatment medium from the treatment feature 130.

As shown in FIG. 5, the body portion 114 may be elongate and cylindrical (e.g., with a round, or circular transverse cross-section, or another shape as desired). As shown, the body portion 114 has a substantially continuous, or constant outer diameter, although the body portion 114 may be tapered or otherwise have a varying diameter as desired. For example, the body portion 114 may taper from a first, larger diameter toward the control portion 112 to a second, smaller diameter toward the tip portion 110. The body portion 114 is generally configured to be resiliently deflectable as it traverses the anatomy of a fistula so that the insert 100 can deflect to accommodate the anatomy of fistulas having a variety of tortuosities. And, the body portion 114 generally has sufficient column strength to permit inserting, or pushing, the body portion 114 through the fistula tract without the body portion 114 kinking or collapsing. For example, in some examples the body portion 114 is configured to bend 90 degrees in one or more directions without kinking. The body portion 114 may be sufficiently flexible, or deflectable to permit traversing the fistula without any substantial damage to surrounding tissue.

The body portion 114 extends between the tip portion 110 and the control portion 112, where the body portion 114 and the tip portion 110 combine to define an insert length of the insert 100. Generally, the insert length represents the length of the insert 100 available to be inserted into a fistula and/or the guide tube 200. The body portion 114 is generally flexible enough in a lateral direction, or laterally, to track the fistula and stiff enough in a longitudinal, or columnar direction to permit pushing the insert 100 through the fistula to get the tip portion 110 to the desired location in the anatomy. In some examples, the body portion 114 of the insert 100 is formed of material exhibiting a flexural modulus of about 250 MPa, between 100 and 500 MPa, or any value or range of values between the foregoing values, and a kink radius of about 15 mm, between 10 mm and 20 mm, or any value or range of values between the foregoing values, although a variety of additional values for flexural modulus and kink radius are contemplated. In some examples, the body portion 114 is configured to exhibit sufficient flexibility that the insert 100 is capable of passing through a fistula having a tortuosity ratio of about 2, or at least 2, although a variety of values are contemplated. Generally, a tortuosity ratio of a fistula having a first end and a second end can be defined as a ratio of a length of the fistula between the first and second ends to a straight-line distance between the first and second ends of the fistula. In some examples, the body portion 114 of the insert 100 is characterized by a buckling force of at least 5 N, although a variety of values are contemplated.

Figure 7A:
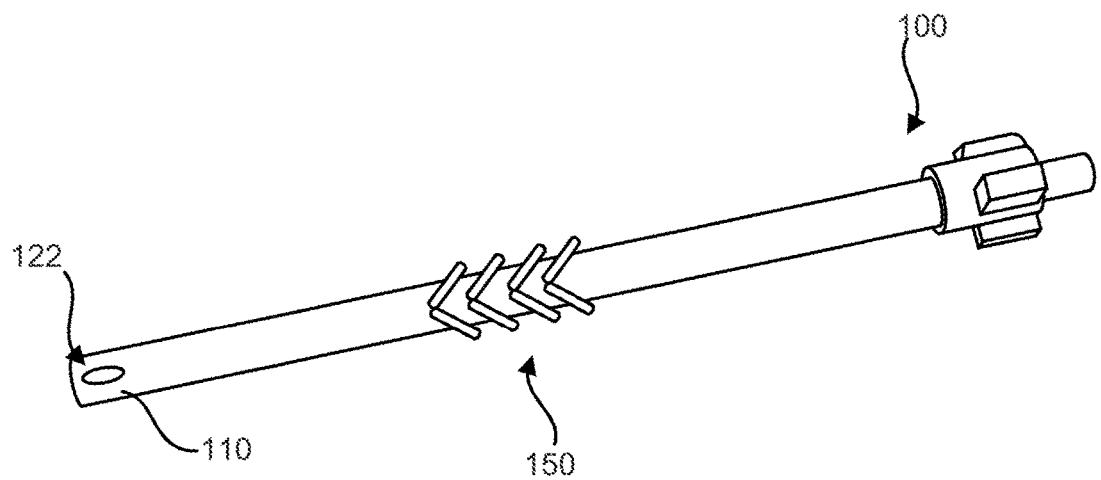
FIGS. 7A to 7C show various features and configurations for a body portion of the insert, according to some embodiments.

Apart from facilitating insertion of the tip portion 110 into a patient, the body portion 114 may include a treatment feature 150 such as that shown in FIG. 7A (e.g., in addition to, or as an alternative to those of the tip portion 110 previously described). FIG. 7A shows one example of the treatment feature 150. As shown, the treatment feature 150 includes a plurality of flexible fingers, or projections that extend out radially from adjacent parts of the body portion 114, and may optionally be angled in a proximal direction, toward the control portion 112 or in any angular orientation as desired. In some embodiments, the flexible fingers, or projections may be used in a cleansing, or clearing operation by inserting and/or retracting the treatment feature 150 within a fistula similar to treatment feature embodiments described in association with the tip portion 110. The flexible fingers or projections may gently abrade, or scrub the walls of the fistula to remove detritus, or other unwanted matter from the fistula, for example. Thus, the treatment feature 150 of FIG. 7A may alternatively be described as an abrasion, abrading, scrubbing, or cleaning feature as desired.

Figure 7B:
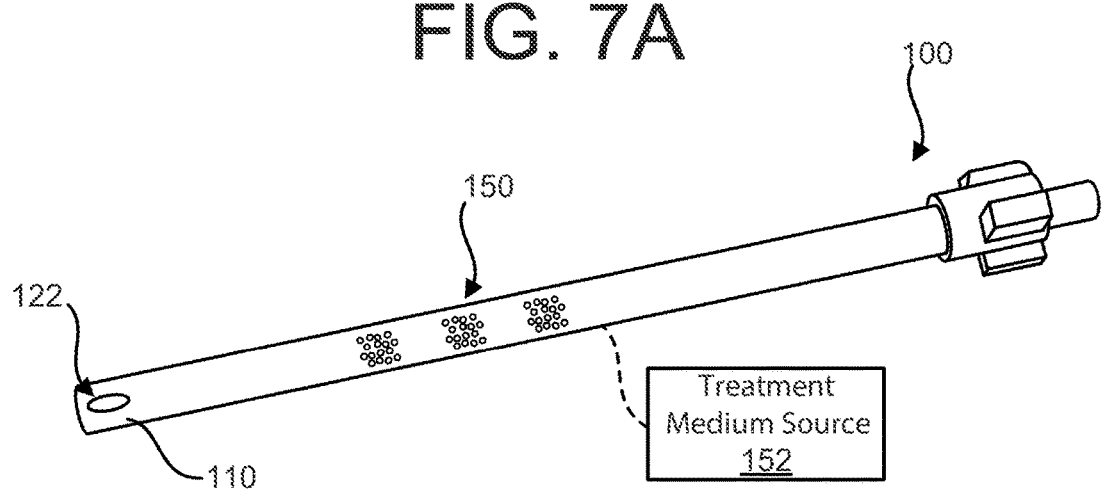

Another example configuration for the treatment feature 150 is shown in FIG. 7B, in the form of one or more fluid apertures (e.g., a plurality of fluid apertures in the body portion 114). As shown, the treatment feature 150 may be in fluid communication with a treatment medium source 152 (e.g., containing water, saline, peroxide, or medicament). The treatment feature 150 may be coupled to the treatment medium source 152 via a variety of methods, but generally one or more lumens, channels, or other features associated with the insert 100 may form a conduit, or pathway from the treatment feature 150 to the treatment medium source 152. In some examples, the treatment medium source 152 is a syringe, or similar apparatus, that may be pressurized to delivery treatment medium from the treatment feature 150.

Figure 7C:
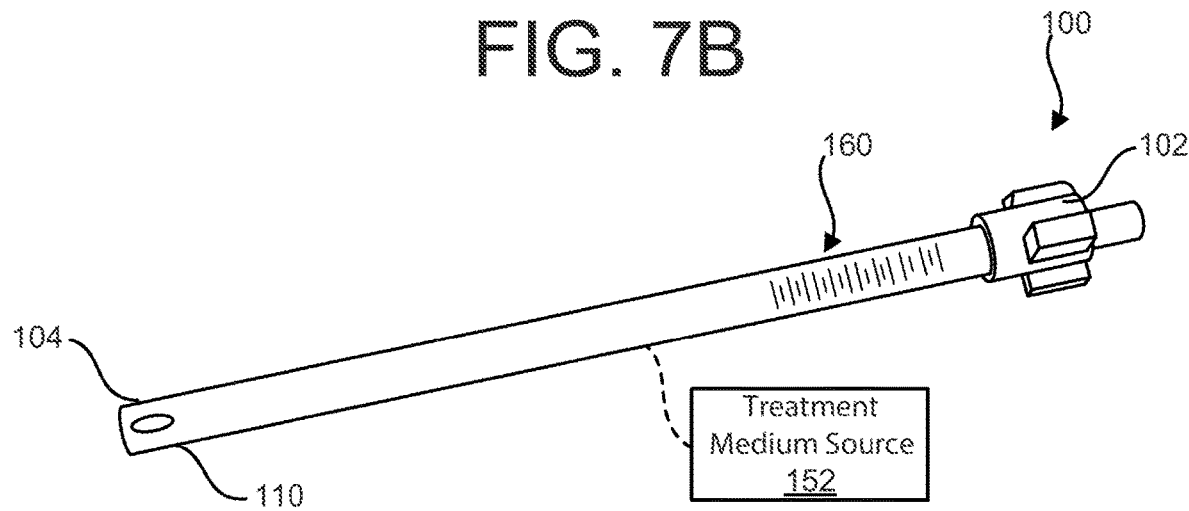
Figure 21:
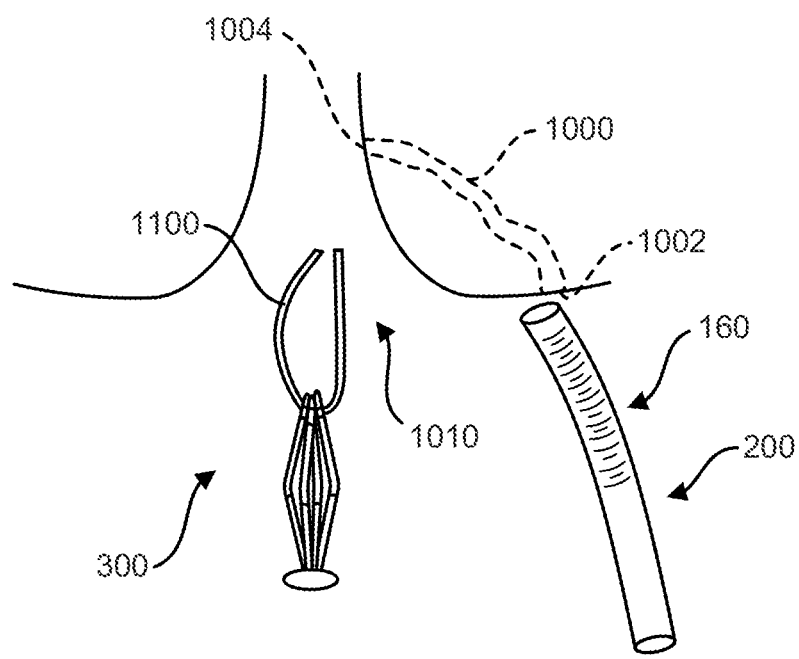
FIGS. 21 to 26 are also representative of an example sequence of delivery of the implant with the system, according to some embodiments.

In still further examples, the body portion 114 additionally or alternatively includes a depth indicator feature 160 as shown in FIG. 7C. As shown, the depth indicator feature 160 may include a series of graduations or other marks that provide information on the depth to which the insert 100 has travelled within the body of a patient (e.g., along a fistula). In some examples, the depth indicator feature 160 can be seen by the unaided eye, and in some examples the depth indicator feature 160 is configured to be observed by means such as fluoroscopy, endoscopy, or ultrasound, for example. Depth indicators 160 may also be placed on other components, for example a guide tube 200 (FIG. 21).

As shown in FIG. 4, the guide tube 200 is an elongate, tubular element that is hollow and defines an internal lumen configured to permit passage of the tip portion 110 and the body portion 114 of the insert 100 through the guide tube 200. The guide tube 200 has a first end 202 and a second end 204 that is located opposite the first end 202, each if which is open to the internal lumen. In some examples, the guide tube 200 and the control portion 112 of the insert 100 are configured to permit passage of the guide tube 200 over the control portion 112. In other examples, the control portion 112 of the insert 100 has a larger diameter than the inner lumen, preventing the insert 100 from passing entirely through the guide tube 200, or in different terms preventing the guide tube 200 from passing entirely over the insert 100. In some examples, the guide tube 200 defines a guide tube length between the first end 202 and the second end 204 that is less than the insert length of the insert 100.

The guide tube 200 is generally flexible enough in a lateral direction to track the fistula and stiff enough in a longitudinal, or columnar direction to permit pushing the guide tube 200 through the fistula. In some examples, guide tube 200 is formed of material exhibiting a flexural modulus of about 250 MPa, between 100 and 500 MPa, or any value or range of values between the foregoing values and a kink radius of 25 mm, between 15 mm and 40 mm, or any value or range of values between the foregoing values, although a variety of additional values for flexural modulus and kink radius are contemplated. In some examples, the guide tube 200 is configured to exhibit sufficient flexibility that the insert 100 is capable of passing through a fistula having a tortuosity ratio of about 2 or at least 2, although a variety of values are contemplated. In some examples, the guide tube 200 is characterized by a buckling force of at least 5 N, although a variety of values are contemplated. In some examples, the guide tube 200 is configured to bend 90 degrees without kinking. In some embodiments, the guide tube 200 is tracked over the insert 100 into the patient. Thus, in some examples, the guide tube 200 may be substantially more flexible than the insert 100 (e.g., being relatively thin-walled). For example, the guide tube 200 can be formed of an extruded and/or wrapped tubular polymeric member. In some examples, the guide tube 200 is formed of a thin, membrane material with relatively high radial, or hoop strength (e.g., expanded polytetrafluoroethylene, or ePTFE).

Though the guide tube 200 may be deployed via insertion into the fistula, in some examples the guide tube 200 is pulled into the fistula, or is delivered via another mechanism. For example, in some methods the guide tube 200 is deployed using an eversion technique, the guide tube 200 being everted by a delivery mechanism into the fistula. U.S. Pat. No. 9,642,693, "Medical apparatus and method of making the same," to Cully et al., describes a delivery system and sleeve that could be modified for this purpose.

As shown in FIG. 2, the implant 300 optionally has a leading portion 302 and a trailing portion 304. In various examples, the trailing portion 304 has an enlarged outer profile relative to the leading portion 302 where the trailing portion 304 of the implant is disc-shaped. As shown, the leading portion 302 of the implant 300 includes a plurality of legs. As described below, in some embodiments, the implant 300 includes a carrier component (e.g., formed of a bioabsorbable material, tissue-derived material) and, optionally, a second component (e.g., active ingredient, cell material, cell-derived material, cellular product material, or hydrolysable material) carried by the carrier component. As described below, the trailing portion 304 of the implant is optionally disc-shaped, the leading portion 302 optionally includes a plurality of legs, and the material forming the implant 300 optionally includes a carrier component (e.g., formed of a bioabsorbable material, tissue-derived material) and a second component (e.g., active ingredient, cell material, cell-derived material, cellular product material, or hydrolysable material) carried by the carrier component.

Implant 300 may take the form of an implantable bioabsorbable device that provides a scaffold to support tissue growth. Devices, such as implant 300 with a scaffold, can be implanted into fistulas to facilitate tissue regeneration and healing of the cavity. For example, cells can migrate into the scaffold, and tissue can be generated as the body gradually absorbs the scaffold material. In various examples, the implant 300 is a fistula plug configured for treating an anal fistula.

A synthetic scaffold (e.g., fistula plug) provided herein such as implant 300 can include randomly arranged fibers comprising polymers of polyglycolic acid (PGA) and trimethylene carbonate (TMC). Any appropriate amount of PGA and TMC can be used to make such synthetic scaffolds. One example of a synthetic scaffold that can be used as described herein is the GORE® BIO-A® Fistula Plug.

In various embodiments, the implant 300 includes the carrier component taking the form of a synthetic scaffold such as that previously described and a second component can include mesenchymal stem cells (e.g., adipose derived mesenchymal stem cells) impregnated into the carrier component to improve efficacy of the implant 300 in treating fistulas (e.g., refractory anal fistulas). In some cases, allogeneic or xenogeneic mesenchymal stem cells (e.g., adipose derived mesenchymal stem cells) can be used instead of autologous cells. Any appropriate method can be used to seed mesenchymal stem cells (e.g., adipose derived mesenchymal stem cells) into such scaffolds. In some examples, one or more therapeutic agents are combined with the scaffold, such as, without limitation, growth factors such as PDGF, FGF, or VEGF, or platelet material such as pooled human platelet derivatives, platelet lysate material, or other cell-derived components such as exosomes, for example.

The leading portion 302 of the implant 300 may include multiple legs to permit a customized fit to various sizes of fistula tracts. That is, one or more of the legs can be trimmed from the leading portion 302 in order to reduce the cross-sectional size of the implant 300 to correlate with the size of the particular fistula tract being treated. Other embodiments of the implant 300 can have a variety of different configurations. For example, in some cases, the implant 300 can be a single elongate element with an elongated conical shape. Further, in some cases, the implant 300 can be a single element with an elongated cylindrical shape. In still other embodiments, the implant 300 may have a variable profile along the length of the device. In general, the implant 300 can be shaped to fill the cavity into which it is implanted and to remain securely implanted therein.

Figure 8:
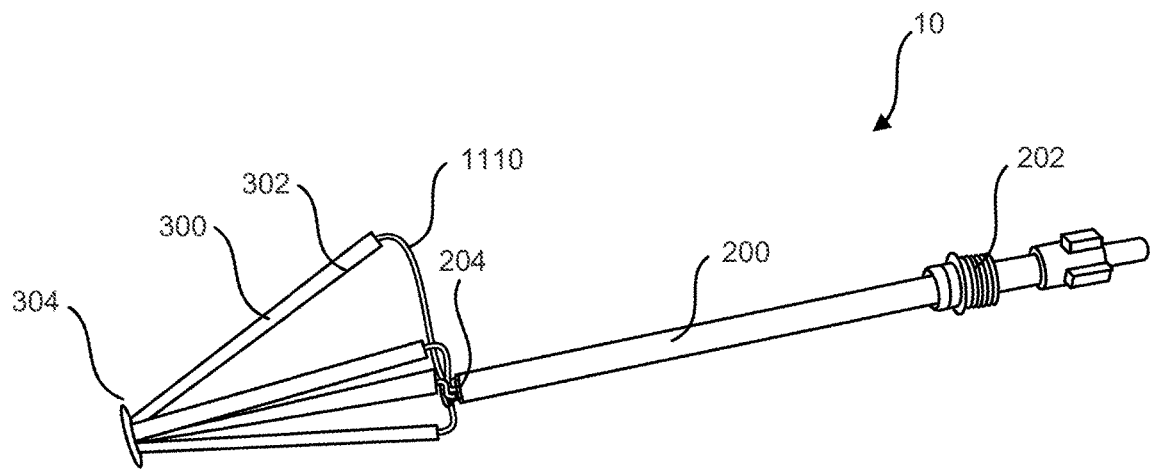
FIGS. 8 to 9 are representative of an example system in various states of assembly, according to some embodiments.
Figure 9:
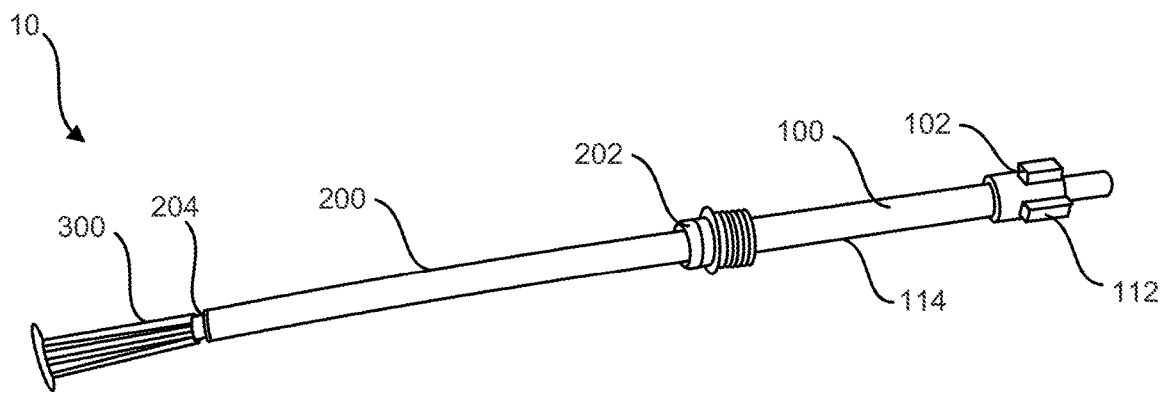

FIGS. 8, 9, and 1 illustrate various states of assembly of the treatment system 10 consistent with methods of treatment. FIGS. 10 to 13 are further illustrations showing the treatment system 10 in the context of patient anatomy, albeit in a generalized form, in the context of a method of treatment using the treatment system 10.

FIG. 8 shows the insert 100 inside the guide tube 200 with the implant 300 attached to the insert 100. FIG. 9 shows the insert 100 partially retracted from the first end 202 of the guide tube 200 with the implant partially retracted into the second end 204 of the guide tube 200. FIG. 1 shows the insert 100 fully retracted from the first end 202 of the guide tube 200 with a tensioning element 1100 (e.g., filament, such as a suture) connecting the implant 300 and the tip portion 110 of the insert 100 exposed from the second end 204 of the guide tube 200. As referenced above, various methods of treatment include one or more of the foregoing steps.

Figure 10:
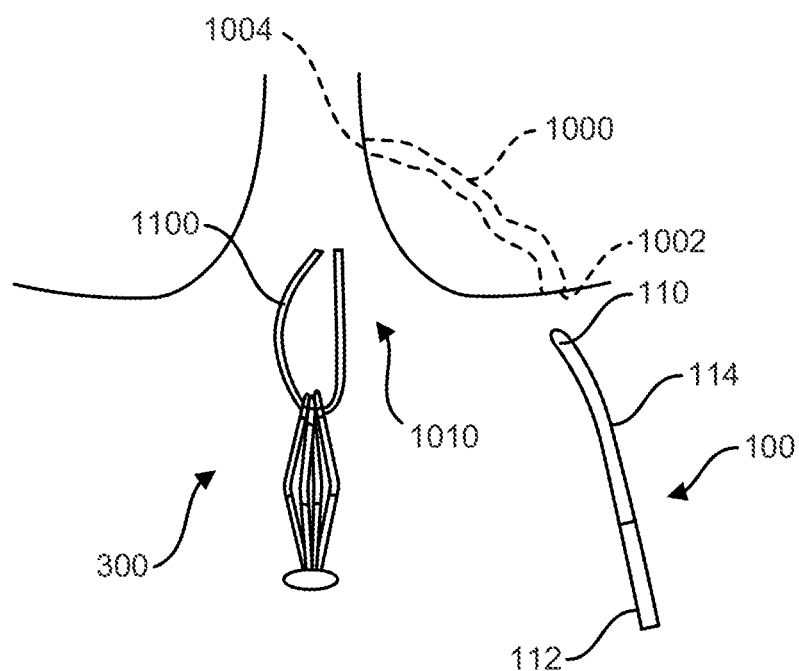
FIGS. 10 to 15 are also representative of an example sequence of delivery of the implant with the system, according to some embodiments.

In general terms, a method of treating a patient using the treatment system 10 may include directing the insert 100 through a fistula 1000 (FIG. 10). The guide tube 200 is placed over the insert 100 either prior to (FIG. 16) or after (FIG. 12 or FIGS. 21-23) directing the insert 100 through the fistula 1000 such that the tip portion 110 of the insert 100 projects from the guide tube 200 (e.g., from the second end 204 of the guide tube 200). The implant 300 is coupled to the tip portion 110 of the insert 100. The insert 100 is retracted such that the implant 300 is pulled into the second end 204 of the guide tube 200. The implant 300 is decoupled from the insert 100, or released from the insert 100. And, the guide tube 200 is removed from the fistula 1000.

As shown schematically in FIG. 10, the fistula 1000 extends between a first end 1002 (e.g., at an external location proximate an anus 1010 of the patient) and a second end 1004 (e.g., internal to a patient, within a GI tract of the patient). Although shown generically in FIG. 10, any of a variety of fistula locations and configurations are possible as will be recognized by those in the field. As shown in FIG. 10, the implant 300 is positioned outside the body of the patient, and the insert 100 is aligned for insertion into the first end 1002 (e.g., an external location proximate the anus 1010) of the fistula 1000.

Figure 11:
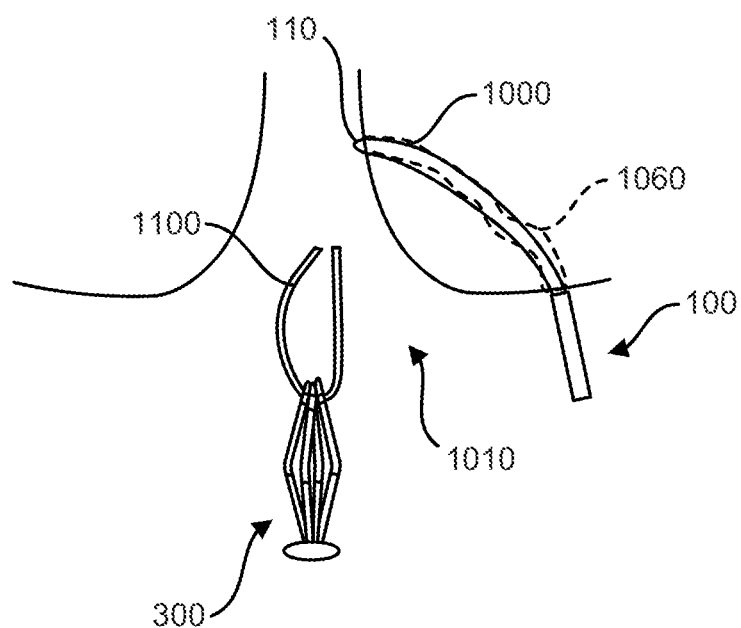

FIG. 11 shows the insert 100 delivered into the first end 1002 of the fistula 1000, optionally, with the tip portion 110 of the insert 100 exposed from the second end 1004 of the fistula 1000. Directing the insert 100 through the fistula 1000 includes tracking a tortuosity of the fistula 1000 with the insert 100. In some embodiments, the insert 100 is used to treat the fistula as previously referenced (e.g., using treatment feature 130 and/or treatment feature 150 such as those previously described). In some embodiments, the fistula is cleansed, cleared, agitated, flushed, medicated, or otherwise treated upon insertion and/or retraction of the insert 100.

Additionally, or alternatively, the insert 100 may be utilized to assess the configuration, or anatomy of the fistula 1000. For example, depth indicator feature 160 may be implemented to determine an overall depth of insertion of the insert 100 into the fistula 1000 to assess a length of the fistula 1000. Additionally, the diameter, length, shape, or other characteristic(s) of the insert 100 may be assessed in the context of whether the insert 100 fits into the fistula 1000 or how well the insert 100 fits into the fistula 1000 to "size" or otherwise characterize the fistula 1000 and assist in selection of an appropriate configuration for the implant 300 (e.g., size, diameter, shape) to be implanted into the fistula 1000. Such assessment may be made based upon the degree of difficulty, or force needed to safely push the insert 100 into the fistula.

Figure 12:
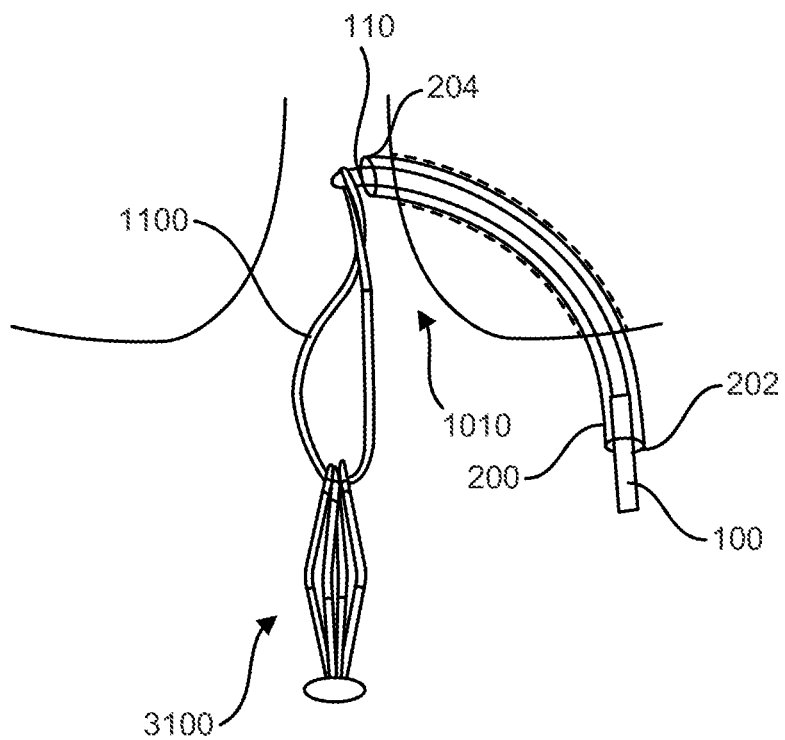

In the example of FIGS. 11 and 12, the guide tube 200 is passed over the insert 100 into the fistula 1000. The insert 100 may act as a reinforcement, and support for the guide tube 200 as it is inserted into the fistula 1000. As previously referenced, in other examples the guide tube 200 has sufficient column strength and flexibility to be first tracked into the fistula 1000, and then the insert 100 may be passed through the guide tube 200 into the fistula 1000 and then attached to the implant 300. In still other examples, the insert 100 is place in the guide tube 200 and the entire assembly is inserted concurrently into the fistula.

As shown in FIG. 12, the insert 100 is received through the guide tube 200 with the implant 300 coupled to the tip portion 110 of the insert 100 using the coupling feature 122. Any of a variety of configurations of the coupling feature 122, including those previously described, may be implemented. The implant 300, and in particular the leading portion 302 of the implant 300, can be sutured or coupled to a filament, line, or other embodiment of the tensioning element 1100 included in the treatment system 10. Coupling the implant 300 to the insert 100 can include connecting a coupling element (e.g., suture, filament, or line) between the tip portion 110 of the insert 100 and the implant 300, although a variety of additional mechanisms (e.g., clamping and hooking arrangements) are contemplated.

In various methods, the leading portion 302 of the implant 300 is introduced into the patient's body (e.g., into the anus) prior to coupling the implant 300 to the tip portion 110 of the insert 100. In some examples, the tensioning element 1100 is first coupled to the implant 300 and then coupled to the insert 100, and in particular the tip portion 110 after the insert 100 is been introduced into the fistula. In various examples, the step of coupling the implant to the insert 100 to the implant 300 includes coupling the leading portion 302 (e.g., a plurality of legs) to the tip portion 110 of the insert 100.

In other examples, the tensioning element 1100 is first attached to the insert 100, and in particular the tip portion 110 of the insert 100, and then following introduction of the insert 100 into the fistula 1000, the implant 300 is coupled to the tensioning element 1100. Regardless, in various examples the coupling feature 122 is utilized to secure the implant to the insert 100 (e.g., directly in the instance of a hooking or clamping feature or indirectly through a tensioning element 1100). It should also be clarified that, in other embodiments, the insert 100 directly captures (e.g., grasps) the implant 300 (e.g., in addition to, or as an alternative to using the tensioning element 1100).

Figure 13:
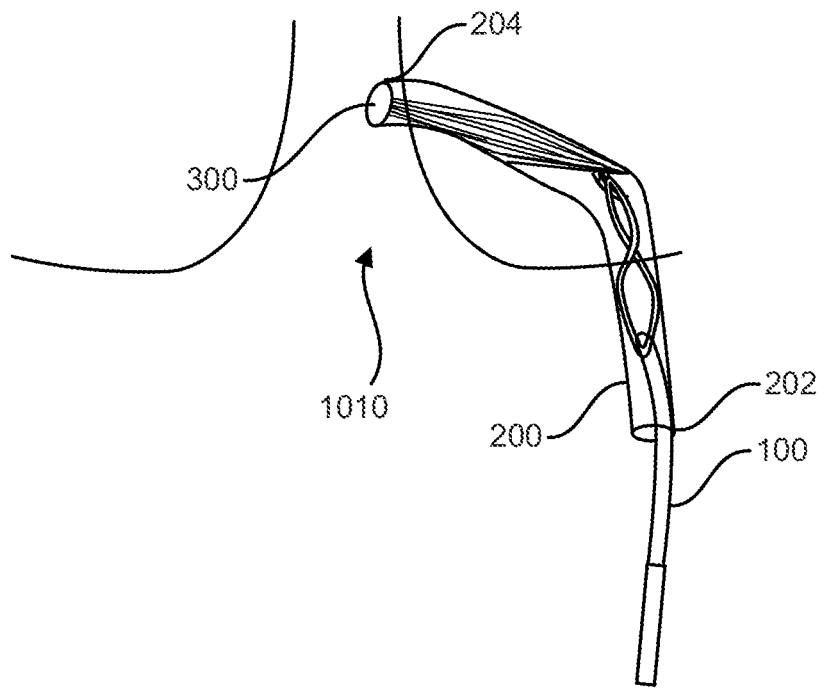

In some examples, retracting the insert 100 such that the insert 100 is pulled into the guide tube 200 includes drawing the trailing portion 304 of the implant 300 into the guide tube 200 prior to removing the guide tube 200 from the fistula 1000. As shown in FIG. 13, as the insert 100 is retracted from the fistula 1000 the implant 300 is drawn into the guide tube 200. In some examples the trailing portion 304 of the implant 300 is drawn to the second end 204 of the guide tube proximal the second end 1004 of the fistula 1000. The trailing portion 304 may have an enlarged profile (e.g., disc-shaped) that can be abutted or engaged with the second end 204 of the guide tube 200 and/or the second end 1004 of the fistula 1000 and seated therewith.

Figure 14:
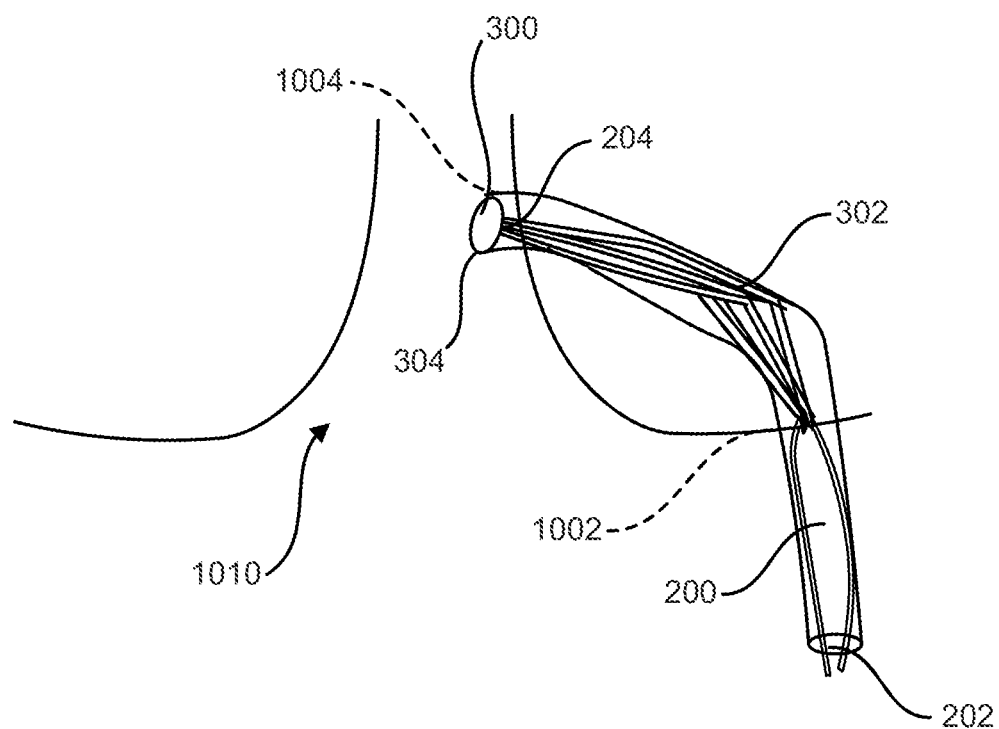
Figure 15:
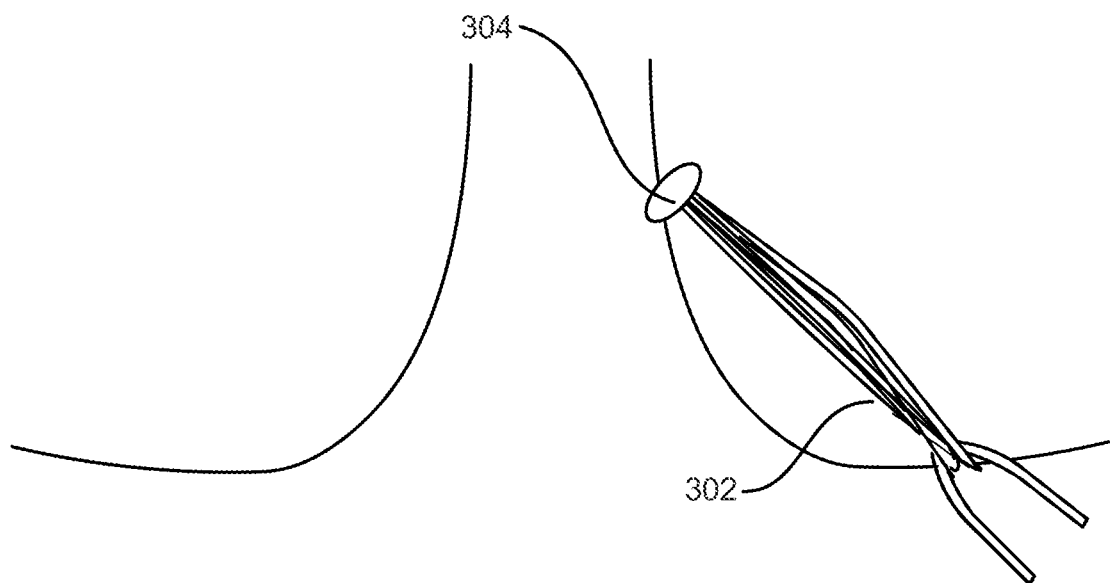

As shown in FIG. 14, the implant 300 and insert 100 are optionally disconnected or otherwise decoupled (e.g., the tensioning element 1100 is optionally severed and removed) and the insert 100 is removed from the patient leaving the insert 100 in place. As shown in FIG. 15, the guide tube 200 may then be removed from the body leaving the implant 300 in the body of the patient. This arrangement can be particularly advantageous, in that the guide tube 200 acts to protect the implant 300 (e.g., the second component, which may be relatively fragile) as it is retracted into the fistula 1000. The guide tube 200 may be treated or otherwise configured to ease introduction of the implant 300 (e.g., being relatively smooth, uniform, having low-friction, hydrophilic coatings and/or other characteristics, for example). This arrangement, using the guide tube 200, can be particularly helpful with implant configurations that have relatively fragile components, as previously referenced.

Figure 16:
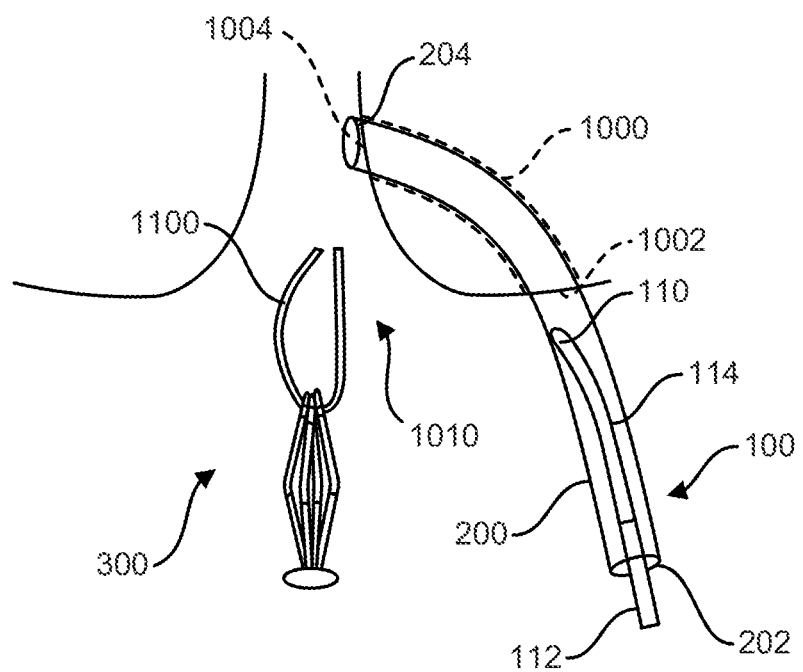
FIGS. 16 to 20 are also representative of an example sequence of delivery of the implant with the system, according to some embodiments.
Figure 17:
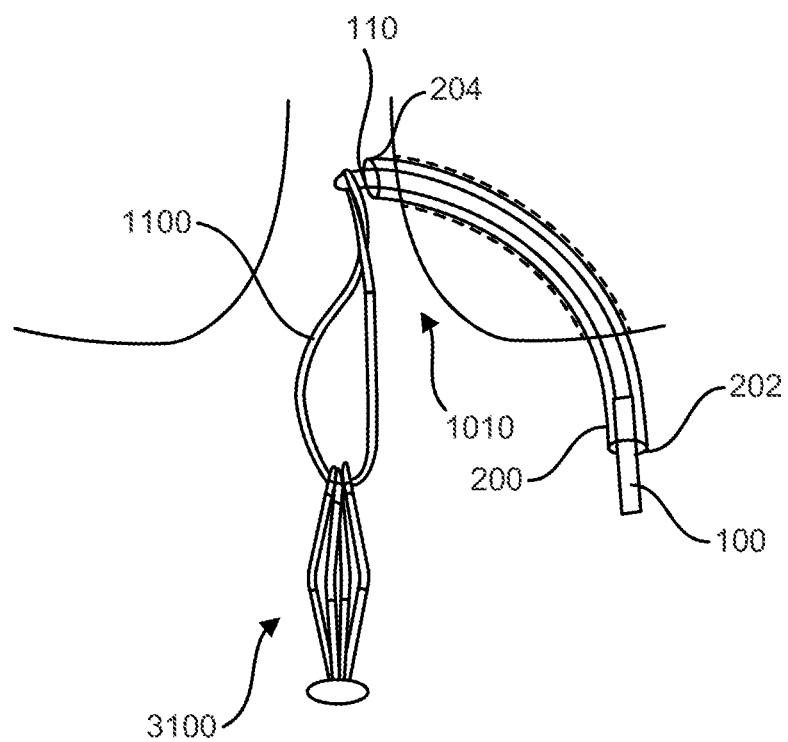
Figure 18:
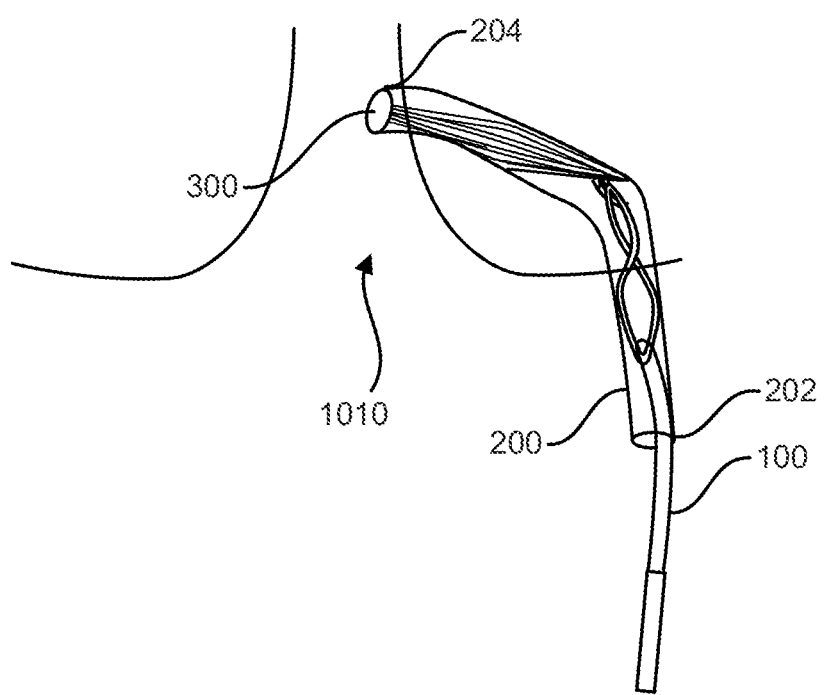
Figure 19:
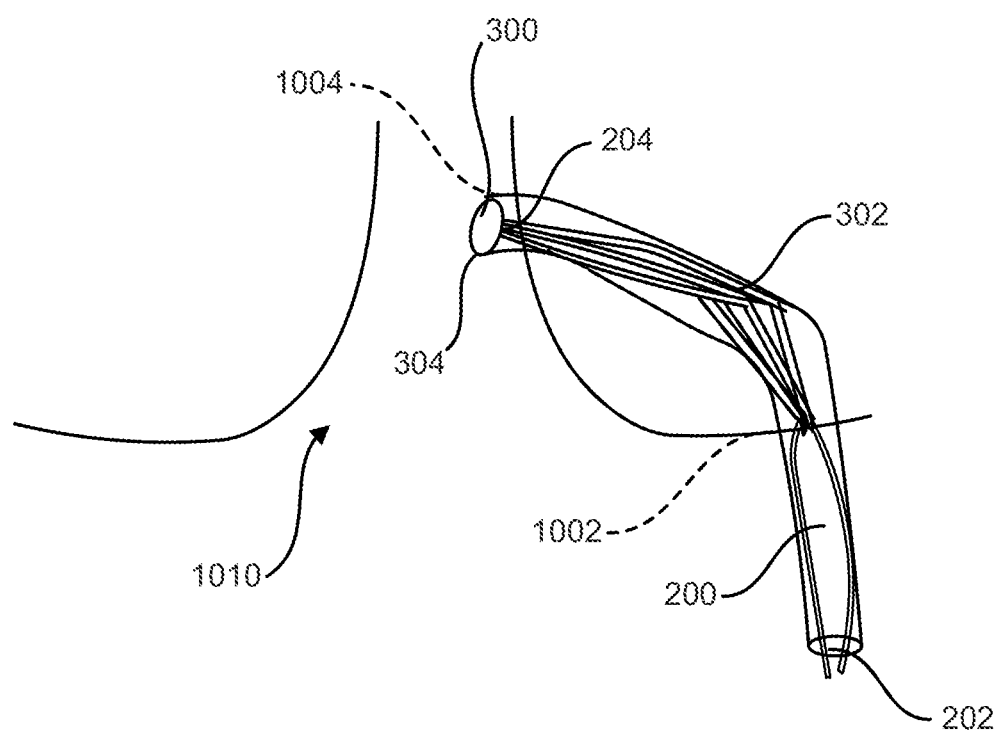
Figure 20:
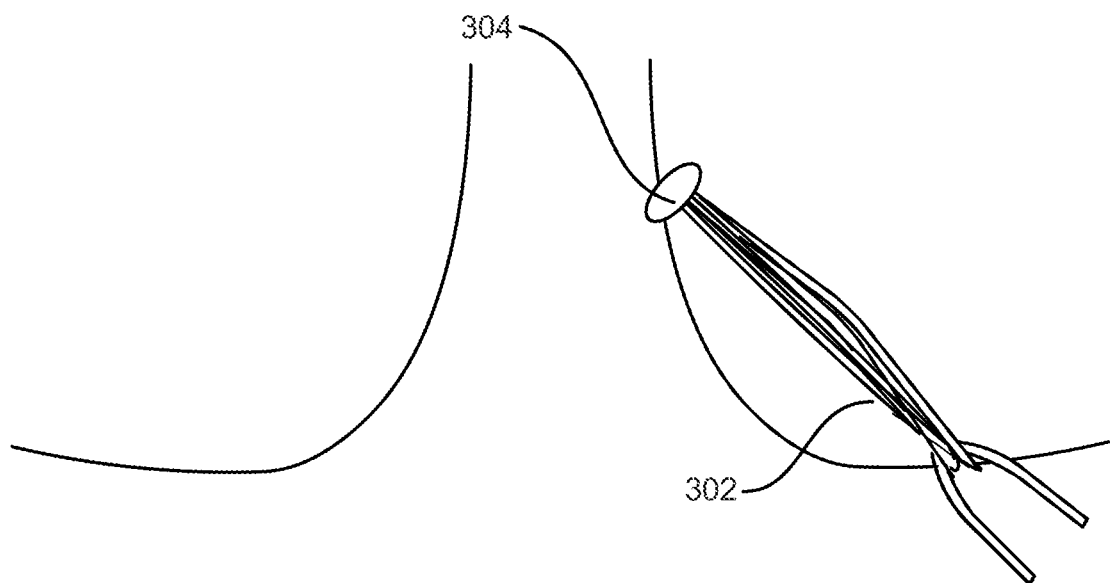

Another method (FIGS. 16-20) of treating a patient using the treatment system 10 may include directing the guide tube 200 through a fistula 1000 (FIG. 16). The insert 100 is positioned in the guide tube 200 during delivery of the guide tube 200 (FIG. 16). The insert is advanced such that the tip portion 110 of the insert 100 projects from the guide tube 200 (e.g., from the second end 204 of the guide tube 200) (FIG. 17). The implant 300 is coupled to the tip portion 110 of the insert 100 (FIG. 17). The insert 100 is retracted such that the implant 300 is pulled into the second end 204 of the guide tube 200 (FIG. 18). The implant 300 is decoupled from the insert 100, or released from the insert 100 (FIG. 19). And, the guide tube 200 is removed from the fistula 1000 (FIG. 20).

Figure 22:
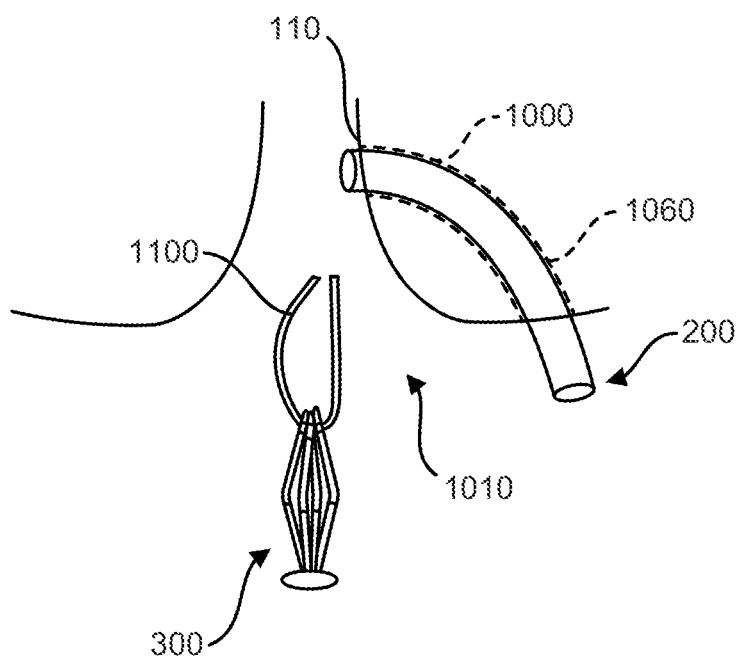
Figure 23:
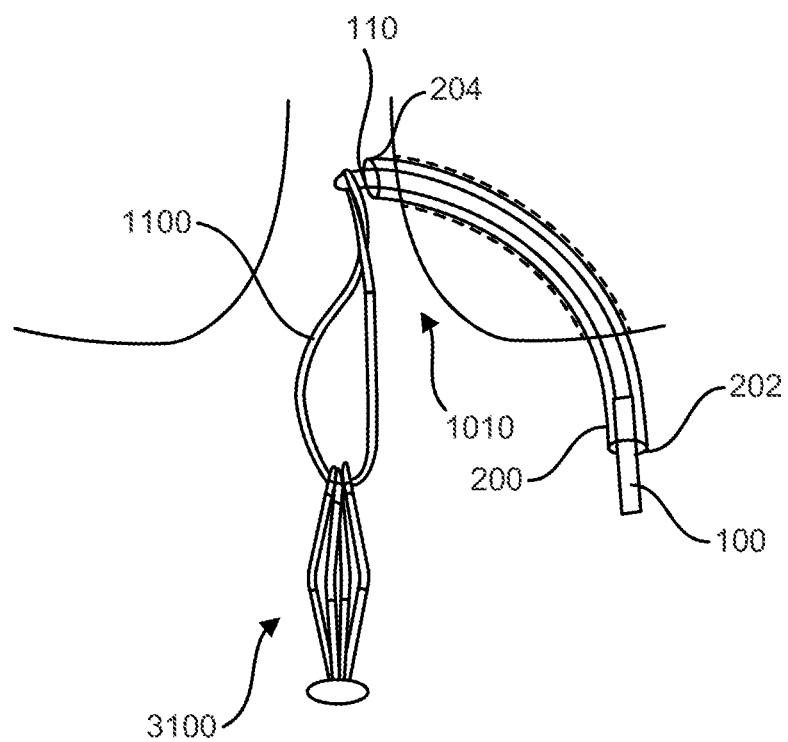
Figure 24:
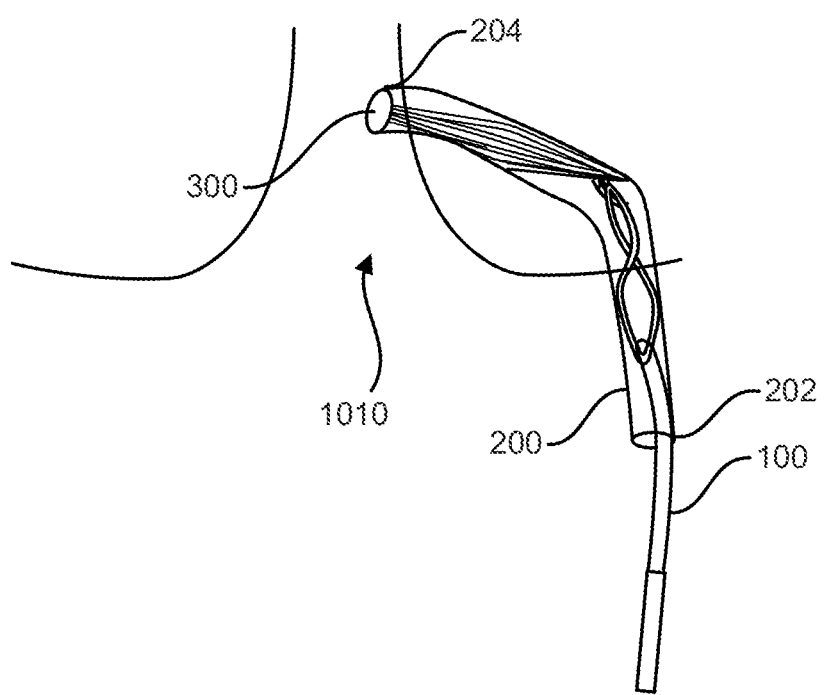
Figure 25:
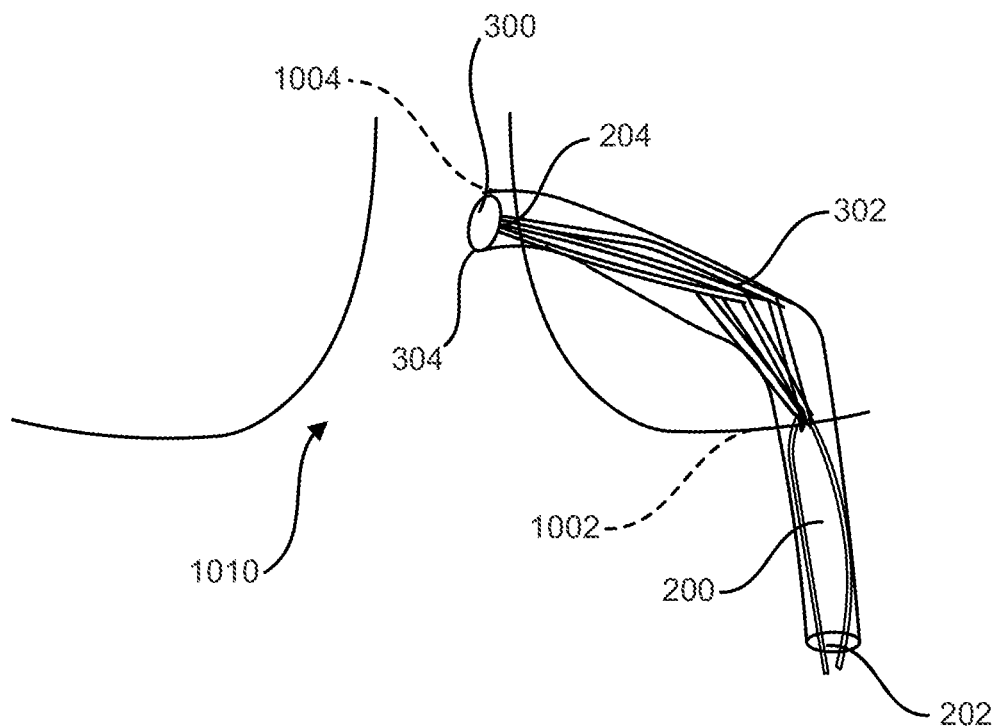
Figure 26:
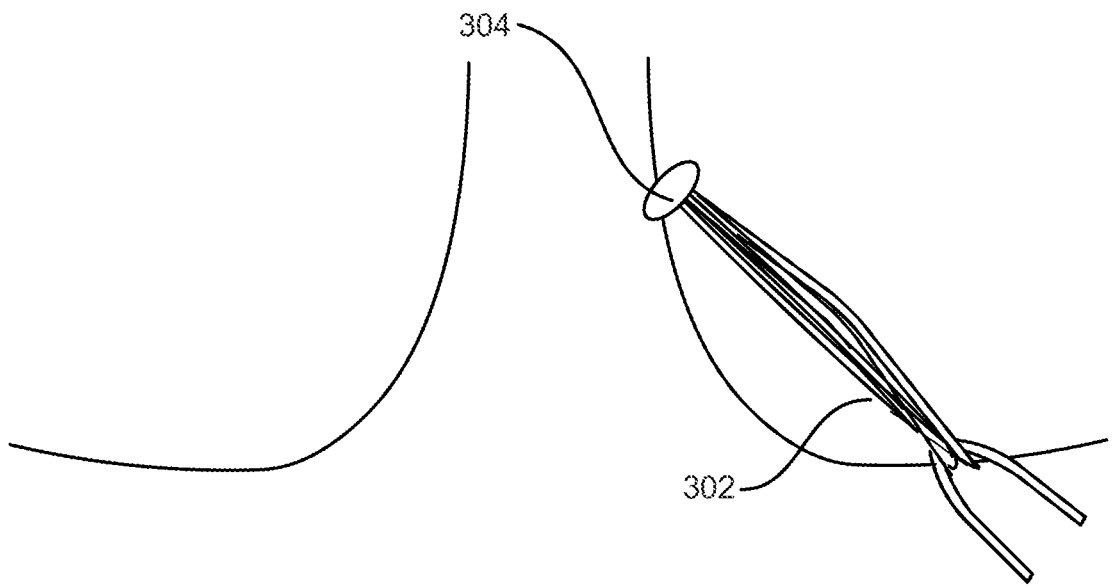

Another method (FIGS. 21-26) of treating a patient using the treatment system 10 may include directing the guide tube 200 through a fistula 1000 (FIGS. 21 and 22). The insert is then guided into the guide tube 200 such that the tip portion 110 of the insert 100 projects from the guide tube 200 (e.g., from the second end 204 of the guide tube 200) (FIG. 23). The implant 300 is coupled to the tip portion 110 of the insert 100 (FIG. 23). The insert 100 is retracted such that the implant 300 is pulled into the second end 204 of the guide tube 200 (FIG. 24). The implant 300 is decoupled from the insert 100, or released from the insert 100 (FIG. 25). And, the guide tube 200 is removed from the fistula 1000 (FIG. 26).

Although the treatment system 10 may include a single insert, guide tube, and/or implant, the treatment system 10 may include a plurality of one or more of the foregoing components. For example, the treatment system 10 may include a plurality of inserts generally similar to the insert 100, with each of the plurality of inserts differing from one another in at least one of length, diameter, curvature, or other feature. In some examples, the treatment system 10 includes a plurality of implants similar to the implant 300, with each of the plurality of implants having at least one of a different diameter, length, and curvature than another one of the plurality of implants. This scenario may be particularly useful where the insert 100 is used to size the fistula 1000 or otherwise be used to pre-select the configuration that would be most desirable for implant 300 out of a variety of configuration choices.

Similarly, some methods of treatment include sizing a fistula using one of the plurality of inserts, each of which is similar to the insert 100, but differ in some respect (e.g., length, diameter, curvature, and/or other feature). In such methods, sizing the fistula includes inserting the insert 100 into a fistula 1000 to make an assessment of the fit of the insert 100 in the fistula 1000 and, optionally, selecting an implant for implantation based upon the assessment; and implanting the implant that is selected based upon the assessment in the fistula 1000.

This patent specification has addressed invention concepts both generically and with regard to specific embodiments. It will be apparent to those skilled in the art that various modifications and variations can be made in the embodiments without departing from the scope of the disclosure. Thus, it is intended that the embodiments cover the modifications and variations those invention concepts provided they come within the scope of the appended claims and their equivalents.

What is claimed is:

1. A treatment system for treating an anal fistula comprising:
    an implant configured for treating an anal fistula having a leading portion and a trailing portion, the trailing portion having an enlarged outer profile relative to the leading portion;
    an insert that is resiliently deflectable, the insert extending between a tip portion and a control portion, with a body portion located between the tip portion and the control portion, the tip portion and the body portion combining to define an insert length of the insert, the tip portion of the insert being configured to be coupled to the leading portion of the implant;
    a guide tube having a distal end and a proximal end, the insert being receivable in the proximal end, the guide tube further having an internal lumen, the guide tube being configured to permit passage of the tip portion and the body portion of the insert through the guide tube, the guide tube having a guide tube length that is less than the insert length; and
    a tensioning element configured to be coupled to the tip portion of the insert and the leading portion of the implant and extending therebetween, such that the implant is retractable into the distal end of the guide tube using the insert with the leading portion of the implant received within the guide tube and the enlarged outer profile of the implant abutted to the distal end of the guide tube.

2. The treatment system of claim 1, wherein at least one of the tip portion and the body portion includes an abrasion feature.

3. The treatment system of claim 1, wherein at least one of the body portion and the control portion includes a depth indicator feature.

4. The treatment system of claim 1, wherein the body portion has a variable diameter.

5. The treatment system of claim 1, further comprising a source of a treatment medium (e.g., water, saline, peroxide, or medicament) in fluid communication with at least one of the tip portion and the body portion and, optionally, wherein at least one of the tip portion and the body portion includes one or more apertures for delivering the treatment medium into a body of a patient.

6. The treatment system of claim 1, wherein the body portion is configured to bend 180 degrees without kinking.

7. The treatment system of claim 1, wherein the tip portion has a taper to a free end.

8. The treatment system of claim 1, wherein the body portion is configured to be resiliently deflectable.

9. The treatment system of claim 1, wherein the trailing portion of the implant is disc-shaped.

10. The treatment system of claim 1, wherein the leading portion of the implant includes a plurality of legs.

11. The treatment system of claim 1, wherein the implant comprises a carrier component (e.g., formed of a bioabsorbable material, tissue-derived material).

12. The treatment system of claim 1, wherein the tip portion of the insert includes an entanglement feature configured to releasably couple to the implant.

13. The treatment system of claim 1, wherein the tip portion of the insert includes an eyelet feature configured to receive a filament coupling the implant to the tip portion and, optionally, wherein the eyelet is formed as an aperture through material of the tip portion or by an adjustable loop.

14. The treatment system of claim 1, wherein the tip portion of the insert includes a hook feature configured to receive a filament coupling the implant to the tip portion.

15. The treatment system of claim 1, wherein the guide tube is substantially more flexible than the insert.

16. The treatment system of claim 1, wherein the body portion of the insert exhibits a flexural modulus between 100 and 500 MPa.

17. The treatment system of claim 1, wherein the guide tube exhibits a flexural modulus between 100 and 500 MPa.

18. The treatment system of claim 1, wherein the body portion is characterized by a buckling force of at least 5 N.

19. The treatment system of claim 1, wherein the implant comprises a carrier component and a second component carried by the carrier component.

20. The treatment system of claim 1, wherein the tensioning element comprises a suture, filament, fiber, or line.

21. A treatment system for treating an anal fistula comprising:
- an implant configured for treating an anal fistula having a leading portion and a trailing portion, the trailing portion having an enlarged outer profile relative to the leading portion;
- plurality of inserts, each insert differing from in at least one of length and diameter, that is resiliently deflectable, each insert extending between a tip portion and a control portion, with a body portion located between the tip portion and the control portion, the tip portion and the body portion combining to define an insert length of each insert, the tip portion of each insert being configured to be coupled to the leading portion of the implant;
- a guide tube having a distal end and a proximal end, each insert being receivable in the proximal end, the guide tube further having an internal lumen, the guide tube being configured to permit passage of the tip portion and the body portion through the guide tube, the guide tube having a guide tube length that is less than the insert length and the guide tube being more flexible than the body portion of each insert; and
- a tensioning element configured to be coupled to the tip portion of each insert and the leading portion of the implant and extending therebetween, such that the implant is retractable into the distal end of the guide tube using each insert, with the leading portion of the implant received within the guide tube and the enlarged outer profile of the implant abutted to the distal end of the guide tube.

22. The fistula implant delivery system of claim 21, wherein the tip portion includes at least one of an eyelet, a hook, and a loop configured for coupling a filament to the tip portion.

23. A treatment system for treating an anal fistula comprising:
- an implant configured for treating an anal fistula having a leading portion and a trailing portion, the trailing portion having an enlarged outer profile relative to the leading portion;
- a plurality of inserts each having at least one of a different diameter, length, and curvature than another one of the plurality of inserts, each insert being resiliently deflectable, and extending between a tip portion and a control portion, with a body portion located between the tip portion and the control portion, the tip portion and the body portion combining to define an insert length, the tip portion being configured to be coupled to the leading portion of the implant, with a tensioning element configured to be coupled to the tip portion of each insert and leading portion of the implant and extending therebetween, such that the implant is retractable into a distal end of a guide tube using the insert, with the leading portion of the implant received within the guide tube and the enlarged outer profile of the implant abutted to the distal end of the guide tube.

24. The treatment system of claim 23, further comprising the guide tube having an internal lumen, the guide tube having a guide tube length that is less than the insert length of, and being configured to permit passage of the tip portion and the body portion of at least one of the plurality of inserts.

25. The treatment system of claim 23, wherein the plurality of inserts each having at least one of a different diameter, length, and curvature than another one of the plurality of inserts.

* * * * *